United States Patent
Bath et al.

(10) Patent No.: US 9,038,631 B2
(45) Date of Patent: May 26, 2015

(54) BREATHABLE GAS APPARATUS WITH HUMIDIFIER

(71) Applicant: ResMed Limited, Bella Vista, New South Wales (AU)

(72) Inventors: Andrew Roderick Bath, Sydney (AU); Geoffrey Crumblin, Sydney (AU); Michael Thomas Janiak, Sydney (AU); Dan Kao, Sydney (AU); Barton John Kenyon, Sydney (AU); Perry David Lithgow, Sydney (AU); Rohan Neil Primrose, Sydney (AU); Jim Saada, Sydney (AU); John Michael Snow, Sydney (AU); Duncan Lovel Trevor-Wilson, Sydney (AU); Alexander Virr, Gosford (AU); Arthur Kin-Wai Yee, Sydney (AU)

(73) Assignee: ResMed Limited, Bella Vista (AU)

( * ) Notice: Subject to any disclaimer, the term of this patent is extended or adjusted under 35 U.S.C. 154(b) by 0 days.

(21) Appl. No.: 14/445,143

(22) Filed: Jul. 29, 2014

(65) Prior Publication Data

US 2014/0332001 A1 Nov. 13, 2014

Related U.S. Application Data

(63) Continuation of application No. 12/659,963, filed on Mar. 26, 2010, which is a continuation of application No. 10/533,940, filed as application No. PCT/AU2004/000810 on Jun. 21, 2004, now Pat. No. 8,006,691.

(30) Foreign Application Priority Data

Jun. 20, 2003 (AU) .................... 2003903139
Sep. 22, 2003 (AU) .................... 2003905136
Feb. 27, 2004 (AU) .................... 2004901008

(51) Int. Cl.
*A61M 15/00* (2006.01)
*F23D 14/00* (2006.01)
(Continued)

(52) U.S. Cl.
CPC ............. *A61M 16/162* (2013.01); *A61M 16/00* (2013.01); *A61M 16/0051* (2013.01);
(Continued)

(58) Field of Classification Search
USPC .......................... 128/200.24, 203.12–203.17, 128/203.26–203.27, 204.14, 128/204.17–204.18, 204.21; 261/130, 142, 261/129, 154, 119, 72.1, DIG. 65; 122/4 A, 122/4 R, 5.5, 7 B, 13.01, 13.3–19.2, 33, 487, 122/DIG. 7
See application file for complete search history.

(56) References Cited

U.S. PATENT DOCUMENTS 1,974,843 A 9/1934 Blashfield
RE19,826 E 1/1936 Aisenstein
(Continued)

FOREIGN PATENT DOCUMENTS

CN 2086150 10/1991
CN 1314192 9/2001
(Continued)

OTHER PUBLICATIONS

Chinese Office Action for co-pending Chinese Application No. 200480017315.1 and English Translation, issued Oct. 9, 2009, 14 pages.
(Continued)

*Primary Examiner* — Rachel Young
(74) *Attorney, Agent, or Firm* — Nixon & Vanderhye P.C.

(57) ABSTRACT

A humidifier has a base unit with an engagement face that is configured to interface with a flow generator. The humidifier also has a tank configured to be removably received by the base unit and hold a volume of liquid. The tank has a side wall with an air inlet. The humidifier further has an air flow passage configured to receive an air connector of the flow generator at the engagement face of the base unit. The air flow passage is axially offset from a tank inlet. In addition, a cross-section of the airflow passage inlet and a cross-section of the tank air inlet are substantially perpendicular to a horizontal plane.

30 Claims, 19 Drawing Sheets

(51) Int. Cl.
*A61M 16/16* (2006.01)
*A61M 16/00* (2006.01)
*A61M 16/10* (2006.01)
*B01F 3/04* (2006.01)
*A62B 9/00* (2006.01)
*B29L 31/00* (2006.01)

(52) U.S. Cl.
CPC ...... *A61M 16/0057* (2013.01); *A61M 16/0066* (2013.01); *A61M 16/16* (2013.01); *A61M 2205/14* (2013.01); *A61M 2205/42* (2013.01); *A61M 2205/50* (2013.01); *A61M 2205/502* (2013.01); *A61M 2205/52* (2013.01); *A61M 2205/6063* (2013.01); *A62B 9/003* (2013.01); *B29L 2031/753* (2013.01); *A61M 16/109* (2014.02); *A61M 2205/36* (2013.01); *B01F 3/0446* (2013.01); *B01F 2003/04872* (2013.01); *B01F 2215/0091* (2013.01)

(56) References Cited

U.S. PATENT DOCUMENTS

| | | |
|---|---|---|
| 2,220,669 A | 11/1940 | Allen |
| 2,598,978 A | 6/1952 | De Martin |
| 2,945,619 A | 7/1960 | Ballard |
| 3,171,353 A | 3/1965 | Mchahan |
| 3,316,910 A | 5/1967 | Davis |
| 3,584,401 A | 6/1971 | Cryer et al. |
| 3,612,710 A | 10/1971 | Mount |
| 3,620,638 A | 11/1971 | Kaye et al. |
| 3,638,926 A | 2/1972 | Melville et al. |
| 3,690,317 A | 9/1972 | Millman |
| 3,806,102 A | 4/1974 | Valenta et al. |
| 3,864,440 A | 2/1975 | Giocoechea |
| 3,954,920 A | 5/1976 | Heath |
| 4,037,994 A | 7/1977 | Bird |
| 4,051,205 A | 9/1977 | Grant |
| 4,105,372 A | 8/1978 | Mishina et al. |
| 4,171,190 A | 10/1979 | Hudson |
| 4,222,971 A | 9/1980 | Eilert |
| 4,229,142 A | 10/1980 | Le Dall et al. |
| 4,237,080 A | 12/1980 | Elliott |
| 4,243,396 A | 1/1981 | Cronenberg |
| 4,336,798 A | 6/1982 | Beran |
| 4,523,896 A | 6/1985 | Lhenry et al. |
| 4,532,088 A | 7/1985 | Miller |
| 4,576,616 A | 3/1986 | Mottram et al. |
| 4,621,632 A | 11/1986 | Bartels et al. |
| 4,629,590 A | 12/1986 | Bagwell |
| 4,644,790 A | 2/1987 | Mizoguchi |
| 4,657,713 A | 4/1987 | Miller |
| 4,676,237 A | 6/1987 | Wood et al. |
| 4,753,758 A | 6/1988 | Miller |
| 4,767,576 A | 8/1988 | Bagwell |
| 4,789,388 A | 12/1988 | Nishibata |
| 4,799,287 A | 1/1989 | Belanger |
| 4,802,819 A | 2/1989 | Bevington |
| 4,807,616 A | 2/1989 | Adahan |
| 4,838,258 A | 6/1989 | Dryden et al. |
| 4,906,417 A | 3/1990 | Gentry |
| 4,913,140 A | 4/1990 | Orec et al. |
| 4,921,642 A | 5/1990 | La Torraca |
| 4,926,856 A | 5/1990 | Cambio et al. |
| 4,941,469 A | 7/1990 | Adahan |
| 4,946,348 A | 8/1990 | Yapp |
| 4,953,546 A | 9/1990 | Blackmer et al. |
| 4,973,234 A | 11/1990 | Swenson |
| 4,993,411 A | 2/1991 | Callaway |
| 5,061,405 A | 10/1991 | Stanek et al. |
| 5,097,424 A | 3/1992 | Ginevri et al. |
| 5,127,800 A | 7/1992 | Hyll et al. |
| 5,231,979 A | 8/1993 | Rose et al. |
| 5,237,987 A | 8/1993 | Anderson et al. |
| 5,271,391 A | 12/1993 | Graves |
| 5,329,939 A | 7/1994 | Howe |
| 5,339,825 A | 8/1994 | McNaughton et al. |
| 5,391,063 A | 2/1995 | Hantle et al. |
| 5,443,061 A | 8/1995 | Champain et al. |
| 5,445,143 A | 8/1995 | Sims |
| 5,482,031 A | 1/1996 | Lambert |
| 5,483,616 A | 1/1996 | Chiu et al. |
| 5,537,997 A | 7/1996 | Mechlenburg et al. |
| 5,551,419 A | 9/1996 | Froehlich et al. |
| 5,558,084 A | 9/1996 | Daniell et al. |
| 5,564,415 A | 10/1996 | Dobson et al. |
| 5,577,496 A | 11/1996 | Blackwood et al. |
| 5,588,423 A | 12/1996 | Smith |
| 5,598,837 A | 2/1997 | Sirianne, Jr. et al. |
| 5,651,775 A | 7/1997 | Walker et al. |
| 5,655,522 A | 8/1997 | Mechlenburg et al. |
| 5,673,687 A | 10/1997 | Dobson et al. |
| 5,682,289 A | 10/1997 | Schwegler et al. |
| 5,794,219 A | 8/1998 | Brown |
| 5,822,715 A | 10/1998 | Worthington et al. |
| 5,828,943 A | 10/1998 | Brown |
| 5,832,448 A | 11/1998 | Brown |
| 5,844,862 A | 12/1998 | Cocatre-Zilgien |
| 5,848,592 A | 12/1998 | Sibley |
| 5,865,171 A | 2/1999 | Cinquin |
| 5,879,163 A | 3/1999 | Brown et al. |
| 5,887,133 A | 3/1999 | Brown et al. |
| 5,888,053 A | 3/1999 | Kobayashi et al. |
| 5,895,595 A | 4/1999 | Haden |
| 5,897,493 A | 4/1999 | Brown |
| 5,899,855 A | 5/1999 | Brown |
| 5,913,310 A | 6/1999 | Brown |
| 5,916,493 A | 6/1999 | Miller et al. |
| 5,918,603 A | 7/1999 | Brown |
| 5,933,136 A | 8/1999 | Brown |
| 5,940,801 A | 8/1999 | Brown |
| 5,943,473 A | 8/1999 | Levine |
| 5,951,300 A | 9/1999 | Brown |
| 5,956,501 A | 9/1999 | Brown |
| 5,960,403 A | 9/1999 | Brown |
| 5,985,559 A | 11/1999 | Brown |
| 5,997,476 A | 12/1999 | Brown |
| D419,658 S | 1/2000 | Matchett et al. |
| 6,023,686 A | 2/2000 | Brown |
| 6,032,119 A | 2/2000 | Brown et al. |
| 6,052,511 A | 4/2000 | Birdsell |
| 6,101,478 A | 8/2000 | Brown |
| 6,109,865 A | 8/2000 | Ishikawa |
| 6,129,524 A | 10/2000 | Woollenweber et al. |
| 6,131,571 A | 10/2000 | Lampotang et al. |
| 6,135,432 A | 10/2000 | Hebblewhite et al. |
| 6,144,837 A | 11/2000 | Quy |
| 6,158,978 A | 12/2000 | Norbury, Jr. |
| 6,161,095 A | 12/2000 | Brown |
| 6,186,140 B1 | 2/2001 | Hoague |
| 6,189,870 B1 | 2/2001 | Withall |
| 6,202,991 B1 | 3/2001 | Coniglio et al. |
| 6,210,116 B1 | 4/2001 | Kuczaj et al. |
| 6,213,119 B1 | 4/2001 | Brydon et al. |
| 6,216,691 B1 | 4/2001 | Kenyon et al. |
| 6,257,171 B1 | 7/2001 | Rivard |
| 6,275,652 B1 | 8/2001 | Chauviaux |
| 6,314,237 B1 | 11/2001 | Glucksman |
| 6,332,462 B1 | 12/2001 | Krohn |
| 6,349,724 B1 | 2/2002 | Burton et al. |
| D454,393 S | 3/2002 | Lynch et al. |
| 6,397,841 B1 | 6/2002 | Kenyon et al. |
| 6,398,197 B1 | 6/2002 | Dickinson et al. |
| 6,435,180 B1 | 8/2002 | Hewson et al. |
| 6,471,493 B2 | 10/2002 | Choi et al. |
| D467,335 S | 12/2002 | Lithgow et al. |
| D468,011 S | 12/2002 | Lynch et al. |
| D468,017 S | 12/2002 | McCombs |
| 6,514,053 B2 | 2/2003 | Takura et al. |
| 6,543,449 B1 | 4/2003 | Woodring et al. |
| 6,546,930 B1 | 4/2003 | Emerson et al. |
| 6,554,260 B1 | 4/2003 | Lipscombe et al. |
| 6,604,390 B1 | 8/2003 | Nooner |
| 6,615,444 B2 | 9/2003 | McGilll et al. |

(56) References Cited

U.S. PATENT DOCUMENTS

| | | |
|---|---|---|
| 6,622,724 B1 | 9/2003 | Truitt et al. |
| 6,669,630 B1 | 12/2003 | Joliat et al. |
| 6,672,300 B1 | 1/2004 | Grant |
| 6,678,215 B1 | 1/2004 | Treyz et al. |
| D487,311 S | 3/2004 | Lithgow et al. |
| 6,718,974 B1 | 4/2004 | Moberg |
| D493,520 S | 7/2004 | Bertinetti et al. |
| D493,884 S | 8/2004 | Virr et al. |
| 6,772,999 B2 | 8/2004 | Lipscombe et al. |
| 6,775,882 B2 | 8/2004 | Murphy et al. |
| D498,527 S | 11/2004 | Virr et al. |
| 6,827,340 B2 | 12/2004 | Austin et al. |
| 6,837,260 B1 | 1/2005 | Kuehn |
| 6,874,771 B2 | 4/2005 | Birdsell et al. |
| 6,896,478 B2 | 5/2005 | Botros et al. |
| 6,910,483 B2 | 6/2005 | Daly et al. |
| 6,918,389 B2 | 7/2005 | Seakins et al. |
| 6,935,337 B2 | 8/2005 | Virr et al. |
| 7,056,289 B2 | 6/2006 | Kasper et al. |
| 7,089,930 B2 | 8/2006 | Adams et al. |
| 7,096,864 B1 | 8/2006 | Mayer et al. |
| 7,111,624 B2 | 9/2006 | Thudor et al. |
| 7,128,729 B2 | 10/2006 | Duchon et al. |
| 7,137,388 B2 | 11/2006 | Virr et al. |
| 7,413,173 B2 | 8/2008 | DiMatteo et al. |
| 7,478,635 B2 | 1/2009 | Wixey et al. |
| 7,614,398 B2 | 11/2009 | Virr et al. |
| 7,616,871 B2 | 11/2009 | Kramer |
| 7,677,246 B2 | 3/2010 | Kepler et al. |
| 8,006,691 B2 | 8/2011 | Trevor-Wilson et al. |
| 2001/0050080 A1* | 12/2001 | Seakins et al. ........... 128/203.16 |
| 2002/0020930 A1 | 2/2002 | Austin et al. |
| 2002/0022973 A1 | 2/2002 | Sun et al. |
| 2002/0056453 A1 | 5/2002 | Klopp |
| 2002/0159897 A1 | 10/2002 | Kegg et al. |
| 2003/0062045 A1 | 4/2003 | Woodring et al. |
| 2003/0065308 A1 | 4/2003 | Lebel et al. |
| 2003/0066526 A1* | 4/2003 | Thudor et al. ........... 128/203.26 |
| 2003/0076745 A1 | 4/2003 | Chapman |
| 2003/0084900 A1 | 5/2003 | Leclerc et al. |
| 2003/0115085 A1 | 6/2003 | Satoh |
| 2003/0187525 A1 | 10/2003 | Mann et al. |
| 2003/0208465 A1 | 11/2003 | Yurko et al. |
| 2003/0236450 A1 | 12/2003 | Kocinski |
| 2004/0035422 A1 | 2/2004 | Truitt et al. |
| 2005/0005937 A1 | 1/2005 | Farrugia et al. |
| 2005/0103339 A1 | 5/2005 | Daly et al. |
| 2005/0217673 A1 | 10/2005 | Daly et al. |
| 2006/0191531 A1 | 8/2006 | Mayer |
| 2006/0237005 A1 | 10/2006 | Virr et al. |
| 2007/0036662 A1 | 2/2007 | Pesola et al. |
| 2007/0134085 A1 | 6/2007 | Daly et al. |
| 2008/0072900 A1 | 3/2008 | Kenyon et al. |
| 2010/0192094 A1 | 7/2010 | Jeha |

FOREIGN PATENT DOCUMENTS

| | | |
|---|---|---|
| DE | 275612 | 1/1913 |
| DE | 275612 | 6/1914 |
| DE | 30 05 094 | 8/1981 |
| DE | 3623162 A1 | 7/1986 |
| DE | 3642637 | 6/1988 |
| DE | 3823242 A1 | 2/1990 |
| DE | 9014848.7 | 3/1991 |
| DE | 4138098 C2 | 11/1991 |
| DE | 4244493 A1 | 7/1993 |
| DE | 93 17 450 | 6/1994 |
| DE | 3789221 | 8/1994 |
| DE | 9409231.1 | 12/1994 |
| DE | 19515739 C2 | 5/1995 |
| DE | 19630466 | 2/1998 |
| DE | 29817685 | 10/1998 |
| DE | 69409024 T2 | 11/1998 |
| DE | 19752672 | 3/1999 |
| DE | 29817685 U1 | 6/1999 |
| DE | 29909611 | 10/1999 |
| DE | 29909611 U1 | 10/1999 |
| DE | 200 13 392 U1 | 10/2000 |
| DE | 100 21 782 | 11/2000 |
| DE | 10016005 | 12/2001 |
| DE | 20213232 | 4/2003 |
| DE | 102005007773 A1 | 9/2005 |
| EP | 0201985 | 11/1986 |
| EP | 0274996 A2 | 7/1988 |
| EP | 0274996 B1 | 7/1988 |
| EP | 0589 429 | 3/1994 |
| EP | 0 760 247 | 3/1997 |
| EP | 0845277 A2 | 6/1998 |
| EP | 0 893 750 | 1/1999 |
| EP | 0903160 A1 | 3/1999 |
| EP | 1 002 552 A2 | 5/2000 |
| EP | 1023912 A2 | 8/2000 |
| EP | 1 055 431 | 11/2000 |
| EP | 1318307 | 6/2003 |
| EP | 1 374 938 | 1/2004 |
| FR | 2 714 985 | 7/1995 |
| GB | 2069607 A | 8/1981 |
| GB | 2177006 A | 1/1987 |
| GB | 2192136 A | 1/1988 |
| GB | 2353904 A | 3/2001 |
| JP | 58-036560 | 3/1983 |
| JP | 64-500088 | 1/1989 |
| JP | 2-19168 | 1/1990 |
| JP | 05-104681 | 4/1993 |
| JP | 6-26894 | 4/1994 |
| JP | 06-190928 | 7/1994 |
| JP | 7-145795 A | 6/1995 |
| JP | 07-03195 | 7/1995 |
| JP | 2293325 | 3/1996 |
| JP | 08-178781 | 7/1996 |
| JP | 09-103490 | 4/1997 |
| JP | 11-398 A | 1/1999 |
| JP | 2000-237316 | 9/2000 |
| JP | 2001-61814 | 3/2001 |
| JP | 2001-160102 | 6/2001 |
| JP | 2001-516277 | 9/2001 |
| JP | 2002-206498 A | 7/2002 |
| JP | 2002-248167 | 9/2002 |
| JP | 2002-253672 | 9/2002 |
| JP | 2002-306601 | 10/2002 |
| JP | 2003-506161 | 2/2003 |
| JP | 2003-527160 | 9/2003 |
| JP | 2004-532666 | 10/2004 |
| WO | 88/00068 | 1/1988 |
| WO | WO 93/05451 | 3/1993 |
| WO | WO 95/15778 | 6/1995 |
| WO | WO 97/32619 | 9/1997 |
| WO | WO 98/31937 | 7/1998 |
| WO | WO 98/33433 | 8/1998 |
| WO | WO 98/41306 | 9/1998 |
| WO | WO 98/57691 | 12/1998 |
| WO | WO 99/13932 | 3/1999 |
| WO | WO 99/22794 | 5/1999 |
| WO | WO 99/64747 | 12/1999 |
| WO | 0021602 | 4/2000 |
| WO | WO 00/27457 | 5/2000 |
| WO | WO 00/32261 | 6/2000 |
| WO | 0038771 | 7/2000 |
| WO | WO 00/42324 | 7/2000 |
| WO | WO 01/10489 A2 | 2/2001 |
| WO | WO 01/32069 | 5/2001 |
| WO | WO 01/73653 A1 | 10/2001 |
| WO | WO 02/02169 A1 | 1/2002 |
| WO | 02/20075 | 3/2002 |
| WO | WO 02/053217 | 7/2002 |
| WO | 02066107 | 8/2002 |
| WO | WO 02/066105 | 8/2002 |
| WO | WO 02/066107 A1 | 8/2002 |
| WO | WO 03/090827 | 11/2003 |
| WO | WO 2005/011556 | 2/2005 |
| WO | WO 2007/019628 | 2/2007 |

(56) References Cited

FOREIGN PATENT DOCUMENTS

| WO | WO 2009/059359 | 5/2009 |
|---|---|---|
| WO | WO 2009/156921 A1 | 12/2009 |
| WO | WO 2010/092496 | 8/2010 |

OTHER PUBLICATIONS

Supplementary European Search Report for Co-pending European Application No. 04737434.3, mailed Oct. 15, 2009, 4 pages.
International Search Report of PCT/AU2004/000810 mailed Oct. 1, 2004.
Office Action and English Translation from copending JP Appln. No. 2006-515549, mailed Jan. 5, 2010, 11 pages.
Office Action and English Translation from copending JP Appln. No. 2006-515549, mailed Nov. 2, 2010, 7 pages.
Office Action from corresponding European Appln. No. 04737434.3, mailed Apr. 14, 2010, 8 pages.
Office Action from corresponding European Appln. No. 04737434.3, mailed Apr. 26, 2010, 8 pages.
Breas Medical AB "iSleep® 20" Brochure, Dec. 2007, 2 pages.
Fisher & Paykel Healthcare "SleepStyle™ 200 CPAP Series" Specification Sheet, 1998, 4 pages.
Fisher & Paykel Healthcare "SleepStyle™ 600 CPAP Series" Specification Sheet, 2005, 4 pages.
Fisher & Paykel Healthcare Two Easy Steps to Comfort, Humidification and Nasal CPAP Therapy, Aug. 1995, 4 pages.
Hoffrichter GmbH "VECTOR therapy in perfection" Brochure, 2002, 2 pages.
MAP Medizin-Technologie GmbH "minni Max nCPAP®, The respiratory therapy device with•out an integrated humidifier", Dec. 2003, 17 pages.
MAP Medizintechnik fuer Arzt und Patient "max II nCPAP moritz II biLevel—The gentle therapy for sleep-related breathing disorders" Brochure, 2000, 4 pages.
Respironics "System One Heated Humidifier User Manual", May 2009, 20 pages.
ResMed, "The SULLIVAN® HumidAire™", 1997, 1 page.
J. H. Emerson Co., Cough Assist, "Non-Invasive Removal of Bronchial Secretions," 2 pages.
Examination Report for copending European Appln No. 04737434.3, mailed Apr. 14, 2010, 8 pages.
Examination Report for copending European Appln No. 04737434.3, mailed Apr. 26, 2010, 8 pages.
German Patient Manual for Hoffrichter/Sandmann CPAP Respirator—Perfect CPAP Therapy, 30 pages plus Translation Verification Certificate, no date, but admitted as prior art prior to critical date.
Kenyon et al., U.S. Appl. No. 12/900,008, filed Oct. 7, 2010.
Kenyon et al., U.S. Appl. No. 12/900,781, filed Oct. 8, 2010.
Hoffrichter Medizintechnik GmbH, "Sandmann CPAP—Therapie in Perfektion" brochure, 32 pages, Mar. 1998.
Madaus Schwarzer Medizintechnik, "New Approaches in Diagnosis and Therapy—Moritz biLevel User Manual", May 1994, 38 pages.
MAP Medizintechnik, "minni Max nCPAP®" brochure, 12 pages, Mar. 2005.
MAP Medizintechnik, "Moritz II biLEVEL®—The gentle therapy for sleep-related breathing disorders" brochure, 6 pages, Jan. 2001.
Photos of MAP Humidifier and Tub, 2 pages and cover sheet, undated.
Madaus Schwarzer Medizintechnik, "New Approaches in Diagnosis and Therapy—Max nCPAP User Manual", Mar. 1994, 38 pages.
ResMed "Sullivan® HumidAire® User's Instructions", 8 pages, undated.
MAP Medizin-Technologie GmbH, Moritz® S/Moritz® ST—Sailing toward therapeutic success . . . , 4 pages, undated.
Hoffrichter "VECTOR CPAP—Therapy With Technical Mastery", 4 pages, Oct. 1998.
Fischer & Paykel, "Two Easy Steps to Comfort", 4 pages, Aug. 1995.
Australian Office Action for corresponding AU Appln. No. 2004248855, Mailed Nov. 6, 2009, 5 pages.
Australian Office Action for corresponding AU Appln. No. 2010201899, Mailed Jun. 10, 2010, 5 pages.
Examiner Summary from Meeting corresponding AU Appln. No. 2010201899, Aug. 12, 2010, 3 pages.
Japanese Office Action and its English Translation for corresponding Japanese Appln. No. 2010-224861, mailed Jan. 18, 2011 (7 pages).
German Patient Manual for Hoffrichter/Sandmann CPAP Respirator—Perfect CPAP Therapy, 30 pages plus Translation Verification Certificate, no date, but admitted as prior to critical date.
Kenyon et al., U.S. App. No. 12/900,008, filed Oct. 7, 2010.
Kenyon et al., U.S. App. No. 12/900,781, filed Oct. 8, 2010.
Japanese Office Action and its English Translation for Corresponding Japanese Appln. No. 2010-224862, mailed Jan. 4, 2011 (9 pages).
Japanese Office Action and its English Translation for Corresponding Japanese Appln. No. 2011-007671, mailed Mar. 1, 2011 (6 pages).
Office Action issued on Jan. 22, 2013 in corresponding Japanese Application No. 2011-201622.
Office Action issued on Mar. 7, 2013 in corresponding New Zealand Application No. 607671.
Office Action issued on Mar. 7, 2013 in corresponding New Zealand Application No. 596207.
Australian Office Action for corresponding Australian Appln. No. 2010257238, mailed Mar. 10, 2011 (2 pages).
Office Action and English Translation for corresponding Japanese Application No. 2006-515549, mailed Mar. 15, 2011, 4 pages.
Proceedings Correspondence issued on Mar. 1, 2012 in corresponding New Zealand Patent No. 567371.
Search Report issued on Jun. 6, 2013 in corresponding European Application No. 11175449.5.
Japanese Office Action (Decision of Rejection) for Application No. 2011-201622 dated Aug. 13, 2013 w/ English Translation (7 pages).
Office Action issued on Sep. 17, 2013 in corresponding Japanese Application No. 2010-153008 (with Translation).
Office Action issued on Oct. 4, 2013 in corresponding Australian Application No. 2013201490.
Office Action issued on Oct. 4, 2013 in corresponding Canadian Application No. 2,753,378.
Office Action issued on Aug. 24, 2012 in corresponding Australian Application No. 2010257238.
Office Action issued on Aug. 7, 2012 in corresponding Japanese Application No. 2010-153008 (with translation).
Office Action of Parent U.S. Appl. No. 10/533,940, filed Dec. 29, 2006, mailed Oct. 12, 2010, 10 pages.
Office Action dated Feb. 25, 2015 issued in U.S. Appl. No. 12/659,963 citing US 6,000,396 and US 5,645,531 (99 pages).
Notification of Second Office Action dated Dec. 24, 2014 issued in Chinese Application No. 201210297972.2 with English-language translation (14 pages).
Office Action dated Feb. 5, 2015 issued in related U.S. Appl. No. 14/445,190 with Form PTO-892 citing U.S. Patent No. 4,025,590 to Igich (32 pages).
Notice of Allowance dated Jan. 13, 2015 issued in U.S. Appl. No. 14/445,152 (35 pages).
Notice of Reasons for Rejection dated Dec. 22, 2014 issued in Japanese Application No. 2014-0006622 with English translation (6 pages).

* cited by examiner

BREATHABLE GAS APPARATUS WITH HUMIDIFIER

CROSS-REFERENCES TO RELATED APPLICATIONS

This application is a continuation of U.S. application Ser. No. 12/659,963 filed Mar. 26, 2010, which is a continuation of U.S. patent application Ser. No. 10/533,940 (issued as U.S. Pat. No. 8,006,691) filed May 4, 2005, which is a national stage application of PCT/AU04/00810, filed Jun. 21, 2004 in English, which claims the benefit of Australian Application No. 2003903139, filed Jun. 20, 2003, Australian Application No. 2003905136, filed Sep. 22, 2003, and Australian Application No. 2004901008, filed Feb. 27, 2004, each incorporated herein by reference in its entirety.

BACKGROUND OF THE INVENTION

This invention relates to breathable gas supply apparatus, and particularly but not exclusively to such apparatus for use in Continuous Positive Airway Pressure (CPAP) treatment of conditions such as Obstructive Sleep Apnea. It will be described herein in its application to CPAP treatment apparatus, but it is to be understood that the features of the invention will have application to other fields of application, such as mechanical ventilation and assisted respiration.

BRIEF SUMMARY OF THE INVENTION

The advantages of incorporating humidification of the air supply to a patient are known, and CPAP machines are known which incorporate humidifying devices. One of the objects of the invention is to provide a simple and compact breathable gas supply apparatus incorporating a humidifier which is simple and economic in its construction, compact, and easy to use. Other objects and advantages of the invention will be described throughout the specification.

It is to be understood that apparatus described herein contains a number of advances on the prior art, many of which independent inventions, although they contribute together to the realisation of the general object expressed above.

The apparatus described herein incorporates novel aspects of architecture which contribute to a reduction in size compared with known units having similar performance. Techniques for noise reduction and damping are described which enable such a smaller machine to have noise performance which is at least as good as known lager machines.

The apparatus described achieves full integration of the humidifier with the flow generator, in the sense that air flow, electrical and, if required, data connection between the flow generator and the humidifier are provided automatically upon the physical engagement of the two devices, without the need for any other process of interconnection.

In such an integrated device, provisions to guard against flowback of water from the humidifier tank to the flow generator are important, and novel sealing arrangements, and novel arrangements for minimising the occurrence of flowback while at the same time improving the uptake of water vapour in the humidifier are also described. The humidifier is readily detached and replaced on the machine, and has very few parts to be disassembled during cleaning.

Also described herein are improved, modular, devices for enabling data connection with the apparatus, including the connection of data storage devices such as memory cards, smart cards, communication ports and the like to be selectively attached by the user or by medical personnel.

The various aspects of the invention will now be described with reference to the accompanying illustrations, which show a presently proposed embodiment.

DETAILED DESCRIPTION OF THE INVENTION

Figure 1:
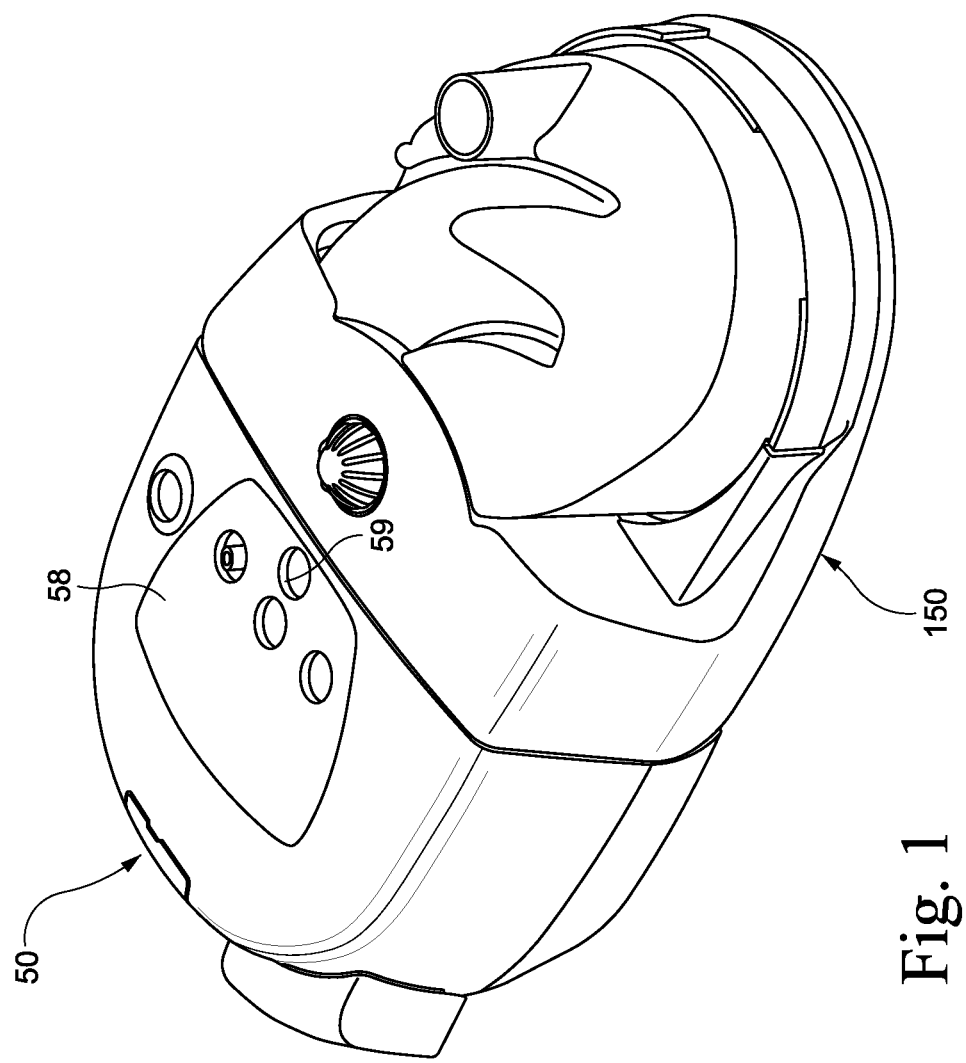
FIG. 1 is a general view of breathable gas apparatus embodying the various features of the invention.
Figure 2:
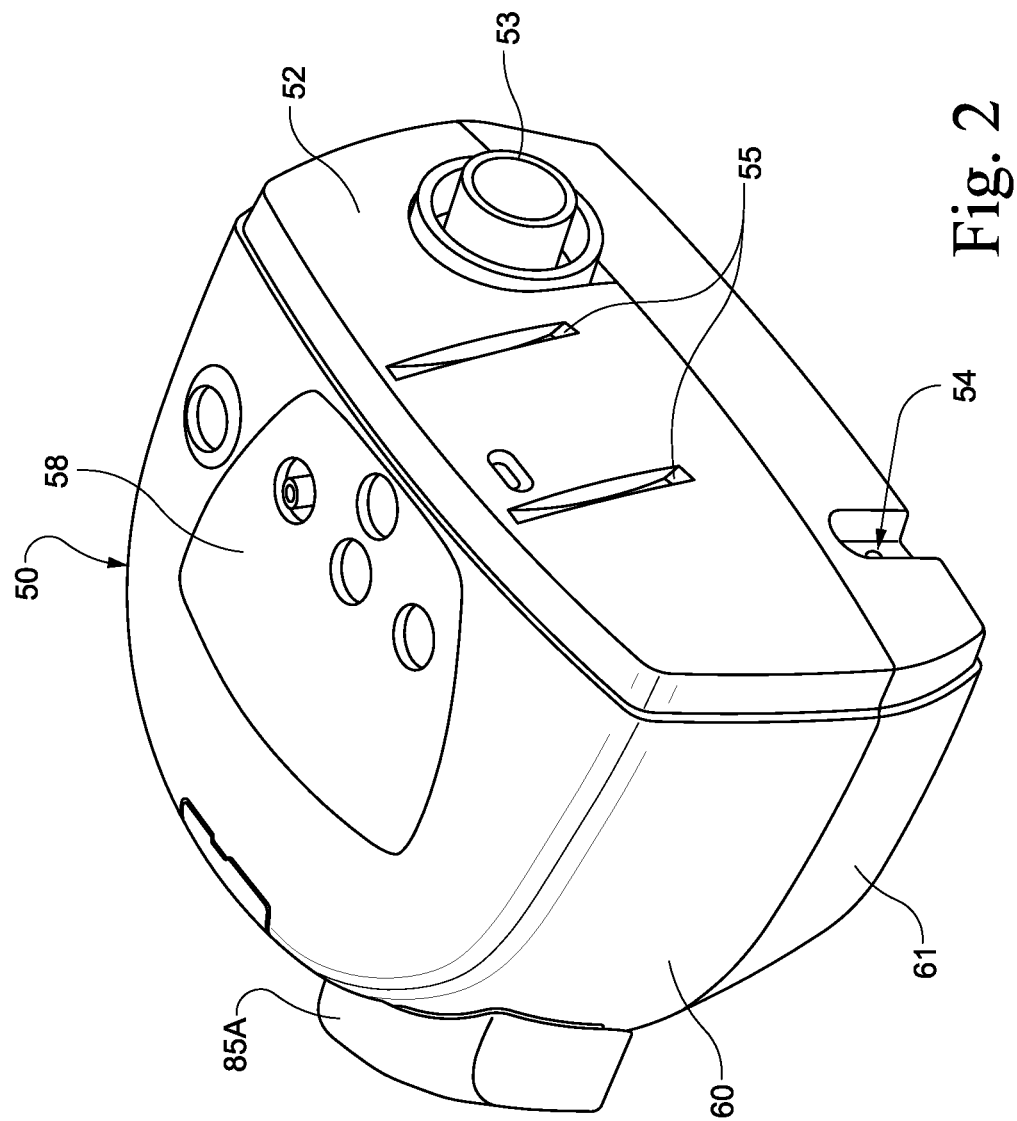
FIG. 2 shows the flow generator of the apparatus.

The illustrated apparatus comprises a flow generator 50 and a humidifier 150, shown in their assembled condition in FIG. 1. As shown in FIG. 2, the flow generator engages with the separable humidifier at an engagement face 52, from which protrudes an air connector 53 for the delivery of air from the fan to the humidifier container, and electrical connectors 54 for the delivery of power to the humidifier heater described below.

Figure 5:
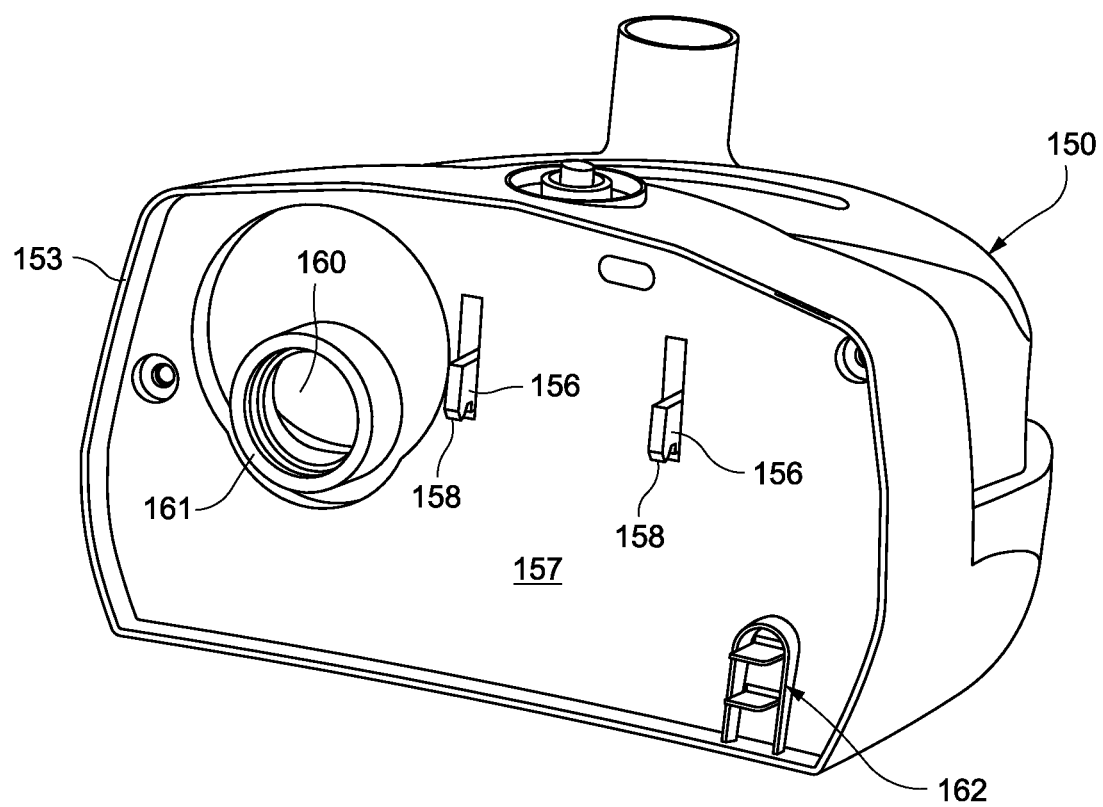
FIG. 5 is a rear view of the humidifier.

The face 52 also carries a pair of slots 55 which are engaged by corresponding tongues 156 provided on the humidifier engagement face 157 (FIG. 5) by which the flow generator 50 and humidifier 150 are connected together, as will be described in more detail below.

Externally, the flow generator 50 is also provided with an LCD screen 58 and associated keys 59 by which the user can set the operating parameters of the unit.

The flow generator 50 has an external case of rigid plastics material moulded in two parts, a top case 60 and a bottom case 61. The lower edge of the top case 60 is stepped and flanged at 62 to mate with the periphery of the bottom case 61. Overmoulded with the rigid plastics body of the bottom case 61 is a rubber sealing flange 63, which locates between and seals against the cases 60 and 61 on the one hand, and the outer surface of a chassis 64 described further below.

Formed in the bottom case 61 by walls which join the outer wall of the case are the lower portions 65 and 67 of, respectively, a power supply cavity and a resonator cavity. The upper portions 66 and 68 of these cavities are formed in the chassis 64, described below.

The chassis 64 is formed with a peripheral wall 69 flanged around its lower edge to engage with the inner periphery of the overmoulded sealing flange 63. The chassis 64 includes a downwardly extending fan cavity 70 in which is mounted the fan 90 described below. This cavity 70 is formed by moulded side walls 71 and base 72, which are formed by moulding thermoplastic around an inserted stainless steel liner 73. The fan cavity 70 opens to the upper surface of the chassis 64 to enable insertion of the fan 90, this opening being closed by a lid 74. Like the cavity 70, the lid 74 has an imbedded stainless steel plate insert moulded within a thermoplastics material, and at its edges the lid is provided with co-molded elastomer sealing edges. The formation of the cavity 70 by insert moulding from differing materials provides very effective acoustic damping, as does the combination by co-moulding of the hard and soft plastics described already and further described below. In this aspect of the present invention, the use of co-moulding or overmoulding in the combination of materials of different, preferably widely different, stiffness and different, preferably widely different, density has been found to be particularly advantageous in providing acoustic damping.

The upper portion 66 of the power supply cavity is formed by a side wall 75 extending downwardly from the roof of the chassis 64, which sealingly engages the opposed wall of the lower portion 65 of this cavity. Preferably, the lower wall is provided for this purpose with a co-moulded or overmoulded rubber sealing flange similar to the sealing flange 63. The power supply compartment is thus sealed against the ingress of moisture from the interior of the unit in the case of backflow from the humidifier. Similarly, the air path is sealed from the power supply compartment. The interior is at the same time acoustically sealed from the power supply cavity, which may not be completely sealed from the exterior, due to the necessity of providing mains power input and low voltage power output to the humidifier, via connectors 54 mounted in apertures 78 and 80 respectively in the rear and front walls of the cavity, and if necessary the venting of the compartment to outside air for cooling.

Supported on the top of the chassis 64, in the space formed between the chassis and the top of the top case 60 is a printed circuit board 81 carrying the electronic control components of the unit. At the rear of the board 81 an edge connector 82 and a sliding connector are accessible from a connector aperture 83 in the rear of the case 60, providing for modular connector arrangements to be described in more detail below.

Also provided in the rear wall of the top case is an air inlet 84, and this communicates with an air inlet passage 85 formed in the roof of the upper portion 66 of the power supply cavity, this passage in turn opening through the inner side wall of that cavity at 87 to the air space surrounding the fan cavity 70 in the interior of the unit. Air drawn into the unit by the fan will thus pass over the roof of the power supply and thereby assist in the dissipation of heat generated by the power supply.

Figure 6:
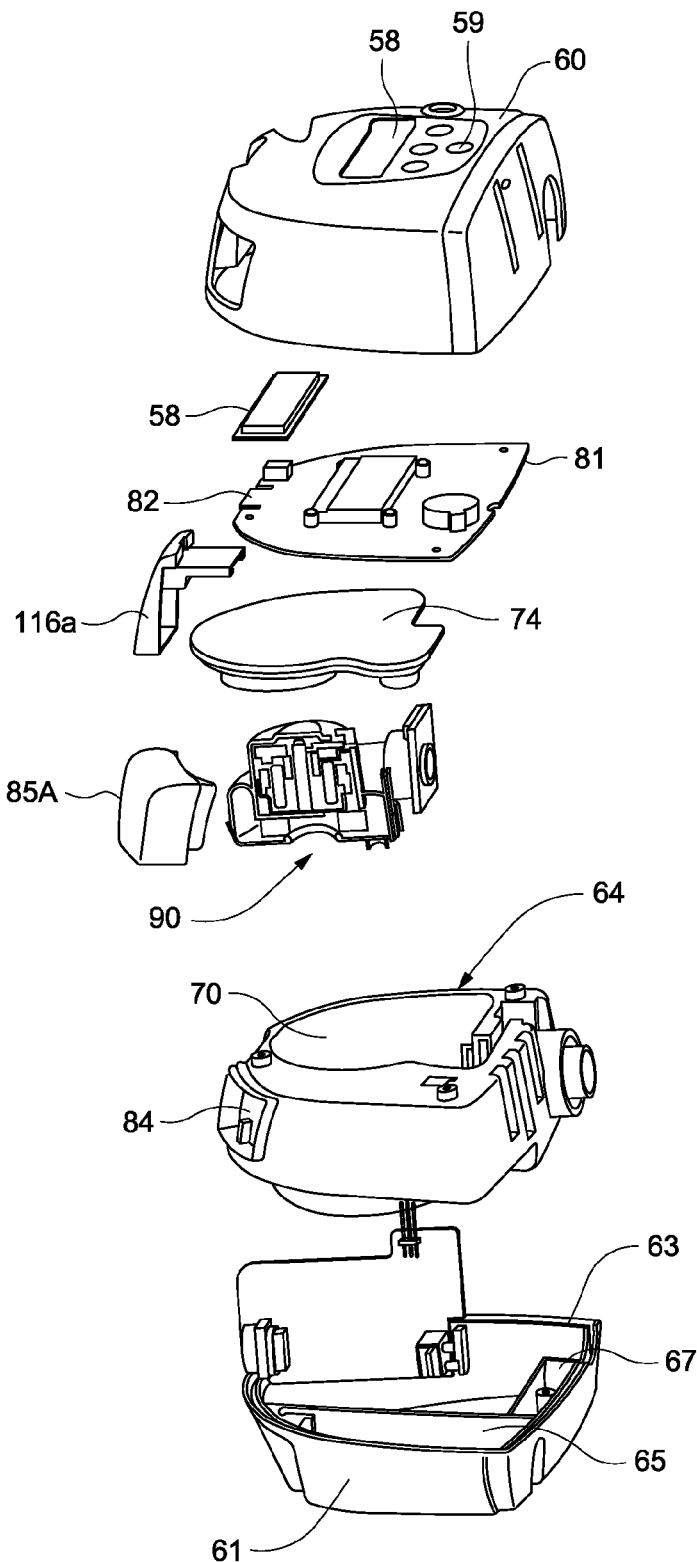
FIG. 6 is an exploded view of components of the flow generator.
Figure 7:
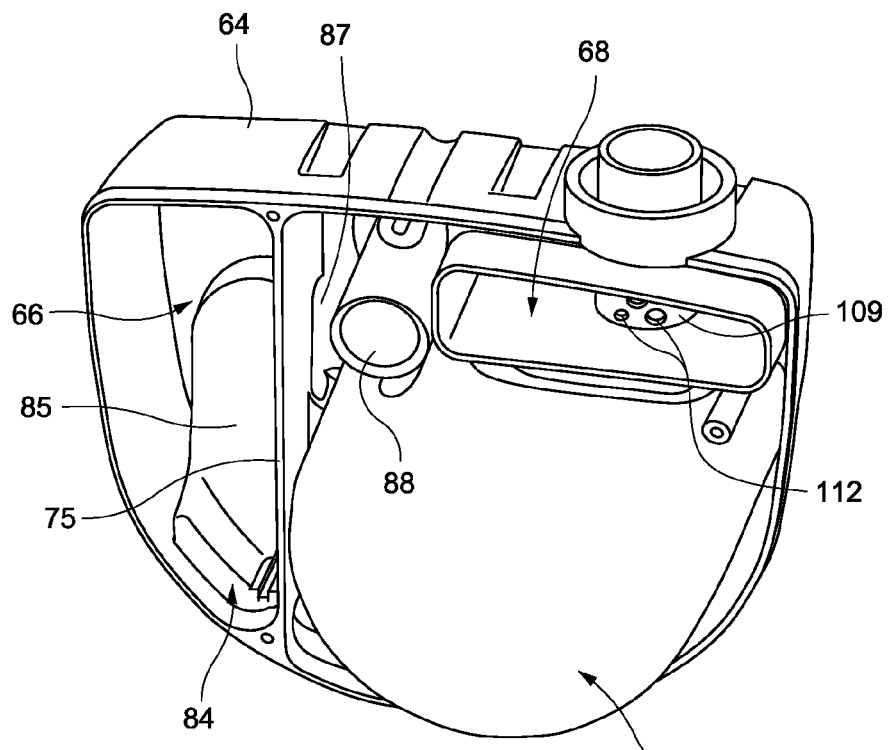
FIG. 7 is an underneath view of a chassis forming part of the flow generator.
Figure 8:
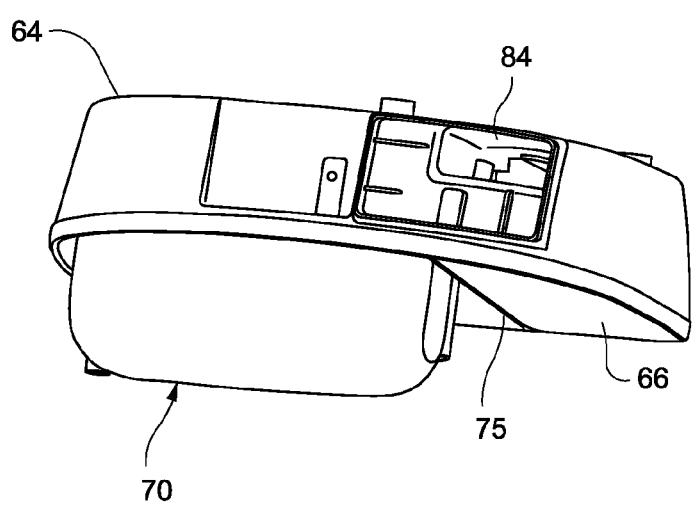
FIG. 8 is a rear view of the chassis.

A removable air filter body 85A containing a replaceable filter element attaches to the inlet 84, as shown in FIGS. 2 and 6.

From the air space surrounding the fan cavity 70, inlet air passes to the fan cavity via an inlet tube 88 depending from a horizontal extension of the side wall 71 of the fan cavity.

The fan cavity and the space surrounding it and enclosed by the upper and lower cases form a pair of serially connected volume mufflers, and the dimensions of the inlet tube 88 and the air passage 85 are chosen to optimise the noise attenuation produced by these mufflers, within the constraint of avoiding unacceptable air flow restriction.

Figure 9:
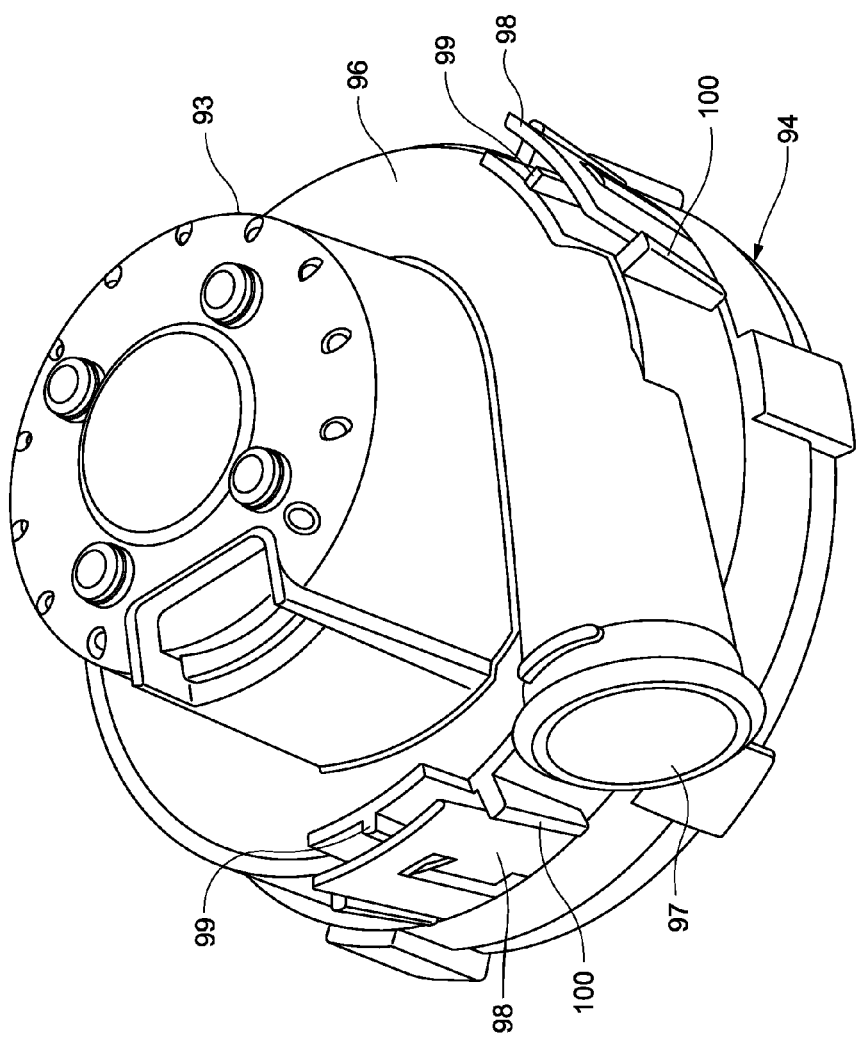
FIG. 9 is a general view of a fan forming part of the flow generator.
Figure 10:
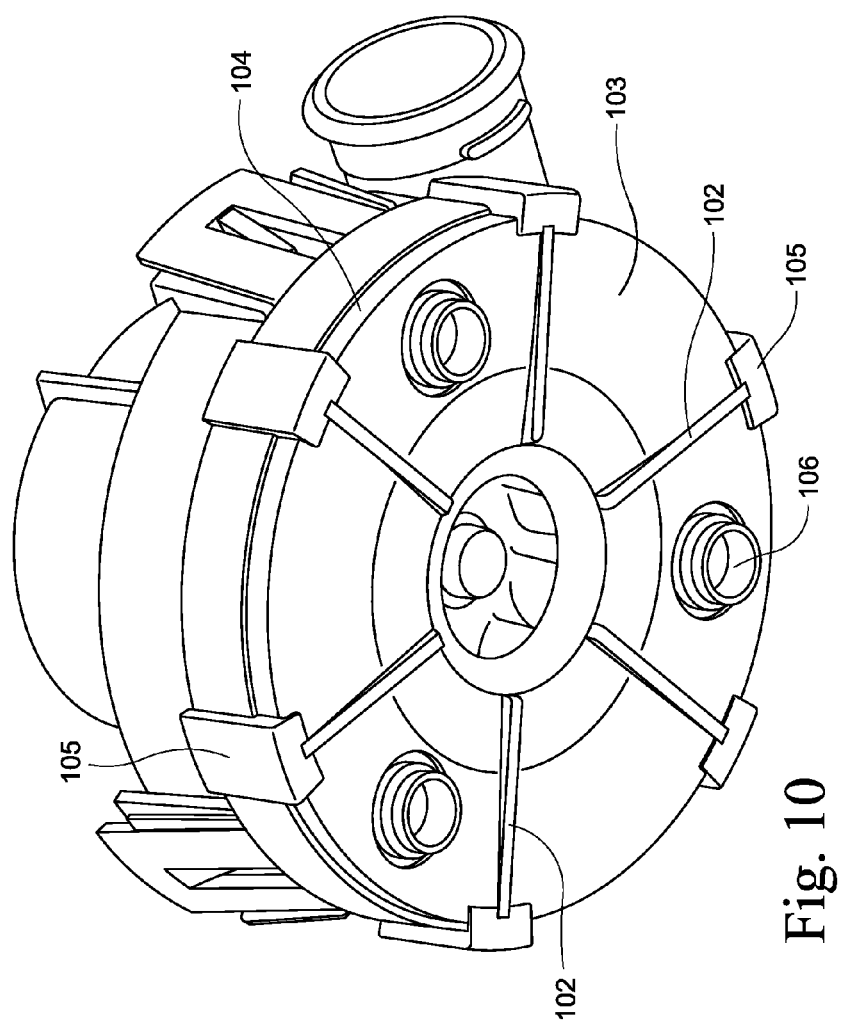
FIG. 10 is an underneath view of the fan.
Figure 11:
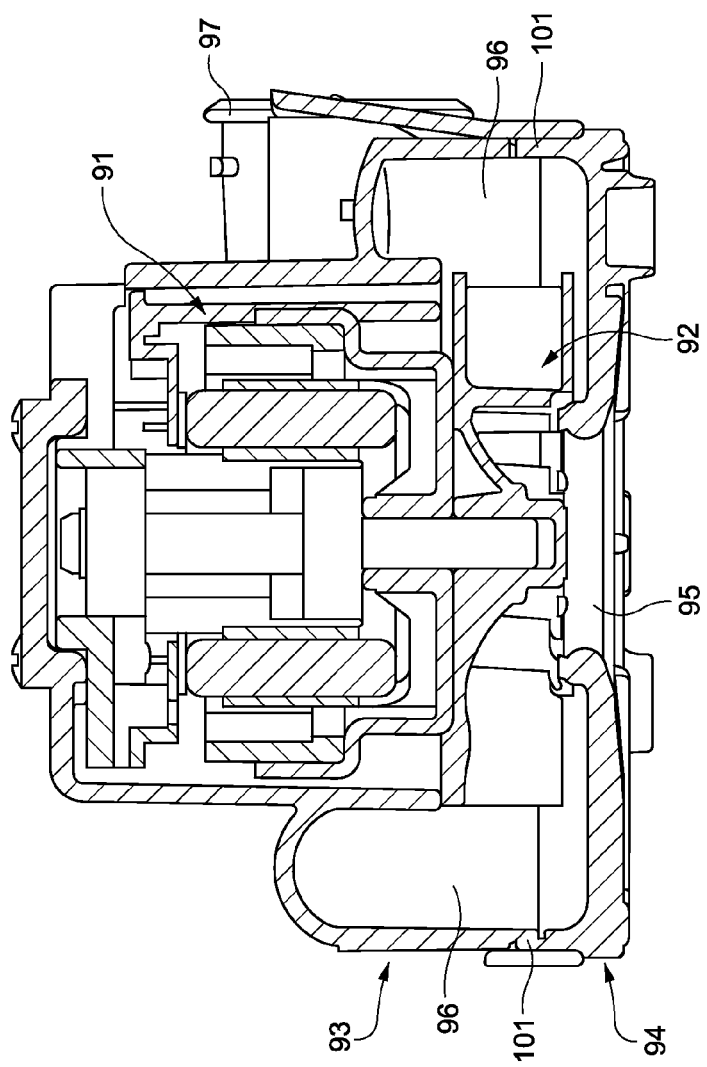
FIG. 11 is a cross-sectional view of the fan.

It will now be convenient to describe the features of the fan, which are shown in FIGS. 9 to 11.

The fan 90 comprises a motor 91, preferably brushless DC motor, provided with a coaxial impeller 92, mounted vertically within a fan housing consisting of a cover 93 and a base 94. An air inlet 95 is provided in the floor of the base 94 on the impeller axis, and cavities in the cover and base form a volute 96 which leads from the impeller to an air outlet 97. The cover and base 93 and 94 are joined by means of slotted tabs 98 which extend upwardly from the base to snap over stepped ribs 99, the tabs 98 being further located by fitting between parallel ribs on the cover 93. The joint between the cover 93 and the base 94 is sealed by an elastomeric sealing ring 101.

The bottom surface of the fan housing base 94 is provided with radial stiffening ribs 102, and overmoulded to the base 94 is an elastomer damping member 103 which covers that bottom surface between the ribs 102, and extends around the edge of the base by a flange portion 104 and peripherally spaced tabs 105. By overmoulding to the rigid plastic base 94 an elastomer of much lower stiffness and much lower density substantial acoustical damping is provided to the fan housing.

Moulded integrally with the rigid plastics portion of the fan housing base are feet 106 which extend through the overmoulded elastomer damping member 103 to receive helical mounting springs (not shown) by which the fan is mounted on the base 72 of the fan cavity.

The degree of size reduction which is an objective of the present invention requires great care to be taken to minimise the transmission of noise and vibration, particularly from the motor and the impeller of the fan 90. The mounting springs are therefore chosen to ensure minimal transmission of the vibration frequencies encountered during operation. This is achieved by choosing the springs with reference to the mass of the fan 90, such that the natural frequency of the system comprising the springs and the fan is at least approximately one tenth of the vibration frequency encountered when the motor is running at its lowest operating speed.

The air outlet 97, upon the introduction of the fan into the fan cavity, is connected by means of a thermoplastic elastomer coupling member with an air outlet passage 109 which extends from the side wall of the fan cavity to a connecting nozzle 110 extending through an aperture 111 provided for this purpose in the front face of the flow generator.

The fan 90 therefore floats within its cavity 70 in the chassis 64 with minimum acoustic coupling to the remainder of the flow generator. The characteristics of the mounting springs and the coupling member are chosen to minimize the transmission of characteristic vibration frequencies of the fan.

The air outlet passage 109 is formed in the roof of the upper portion 68 of the resonator cavity. Holes 112 communicating with the resonator cavity are provided in the floor of the passage 109 where it crosses this cavity, which acts in the manner of a Helmholtz resonator. By adjusting the dimensions and number of the holes 112, the frequency response of the resonator can be adjusted for optimum noise cancellation. If desired, a second Helmholtz resonator cavity can be provided opposite the upper portion 68 of the resonator cavity, if the dimensions of the top case 60 allow this.

The novel use of Helmholtz resonators for noise attenuation contributes to the success in achieving significant size reduction in the flow generator of the present invention.

Figure 12:
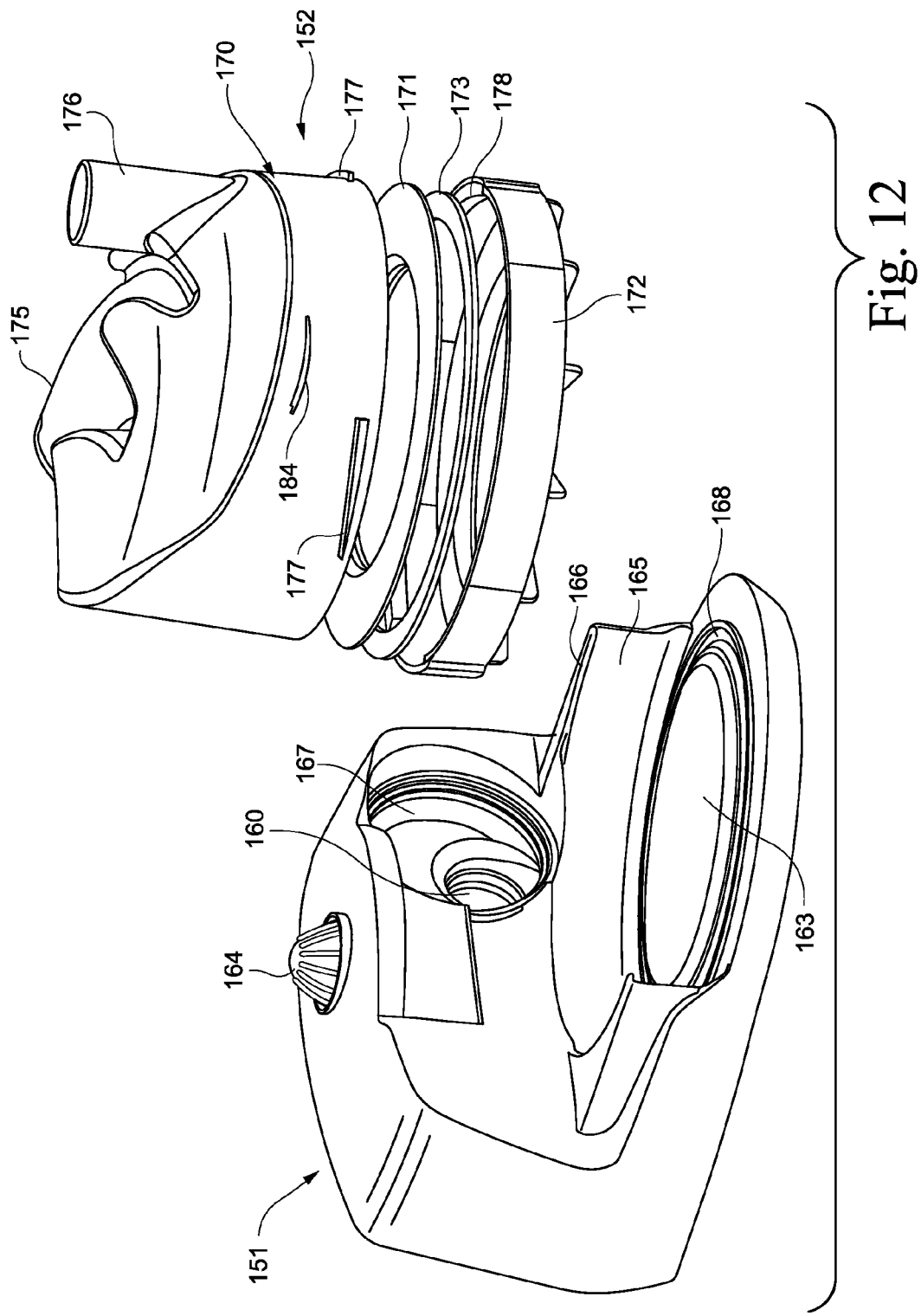
FIG. 12 shows the humidifier in partly disassembled state.
Figure 13:
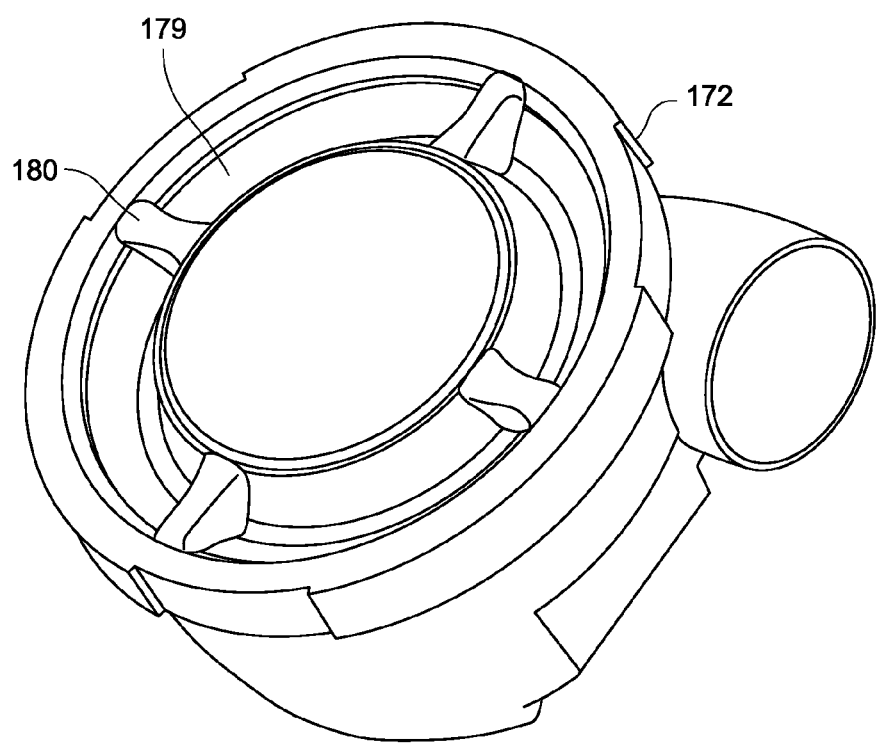
FIG. 13 is an underneath view of the tank of the humidifier.

As shown in FIG. 12, the humidifier 150 comprises a base unit 151 designed for simple attachment to and detachment from the flow generator 50, and a tank 152 which is similarly attachable to and detachable from the base unit.

The rear face of the base unit 151 has a peripheral flange 153 which seats in a corresponding peripheral recess 113 surrounding the front face of the flow generator 50 when the two units are brought together by linear movement towards each other. The tongues 156 are moveable vertically and resiliently urged downwardly, so that these tongues engage in the slots 55 and snap home to engage the two units by means of the downwardly extending fingers 158 at the ends of the tongues.

An air flow passage 160 passes through the humidifier engagement face 157 and opens to the front wall of the base unit. This passage is surrounded at the rear wall with a cylindrical connecting portion 161 which receives the nozzle 110 of the flow generator upon engagement of the two units. The inner surface of the portion 161 is provided with a sealing device such as a layer of elastomer or other soft resilient material.

The rear face of the base unit also carries a connector 162, in this embodiment a pair of flat male blade connectors, for engagement with a mating connector on the front face of the flow generator, to provide power to the humidifier heater from the power supply in the power supply cavity. Although not shown in the illustrated embodiment, the respective faces may also carry further interconnecting devices, where other electrical or data connections are required to be established between the flow generator and the humidifier or downstream devices including the air conduit or the mask. Such devices may take the form of optically coupled devices, or connectors of other suitable kinds.

The use of such an opto-coupling connector enables the implementation of a simple protocol for communications between the flow generator and the humidifier. For example, the current flow levels of the flow generator can be sent to the humidifier controller which then adjusts the operation of the humidifier according to a predetermined algorithm.

Within the humidifier base unit 151 but not shown here is provided a variable power supply for a heating element which heats a circular metal pad 163. A control knob 164 is provided on the upper surface of the unit for adjustment of the heat supplied to the pad 163. A semicircular wall 165 surrounds the rear part of the pad 163, and carries at its upper edge an inwardly directed flange 166. The pad 163 stands proud of the surrounding base surface 168.

It will be observed that the air flow passage 160 opens to the front face of the base unit at the foot of a circular recess 167 of larger diameter, corresponding to the diameter of the tank air inlet 175 described below. The effect of this is to provide a vertical offset between the air flow passage 160 and the inlet 175, with the former lower than the latter in the normal orientation of the unit. This configuration assists in the prevention of backflow as will be described below. It is to be observed that the axial offset in question could be achieved in other ways.

The recess 167 is provided with a sealing layer of elastomer or other sealing material.

The tank 152 comprises a cover 170 which is preferably of a transparent plastics material, a metal base 171 preferably of stainless steel, a base flange 172 which functions to couple the cover and the base, and a sealing gasket 173 which locates between the base of the cover and the metal base 171.

Figure 3:
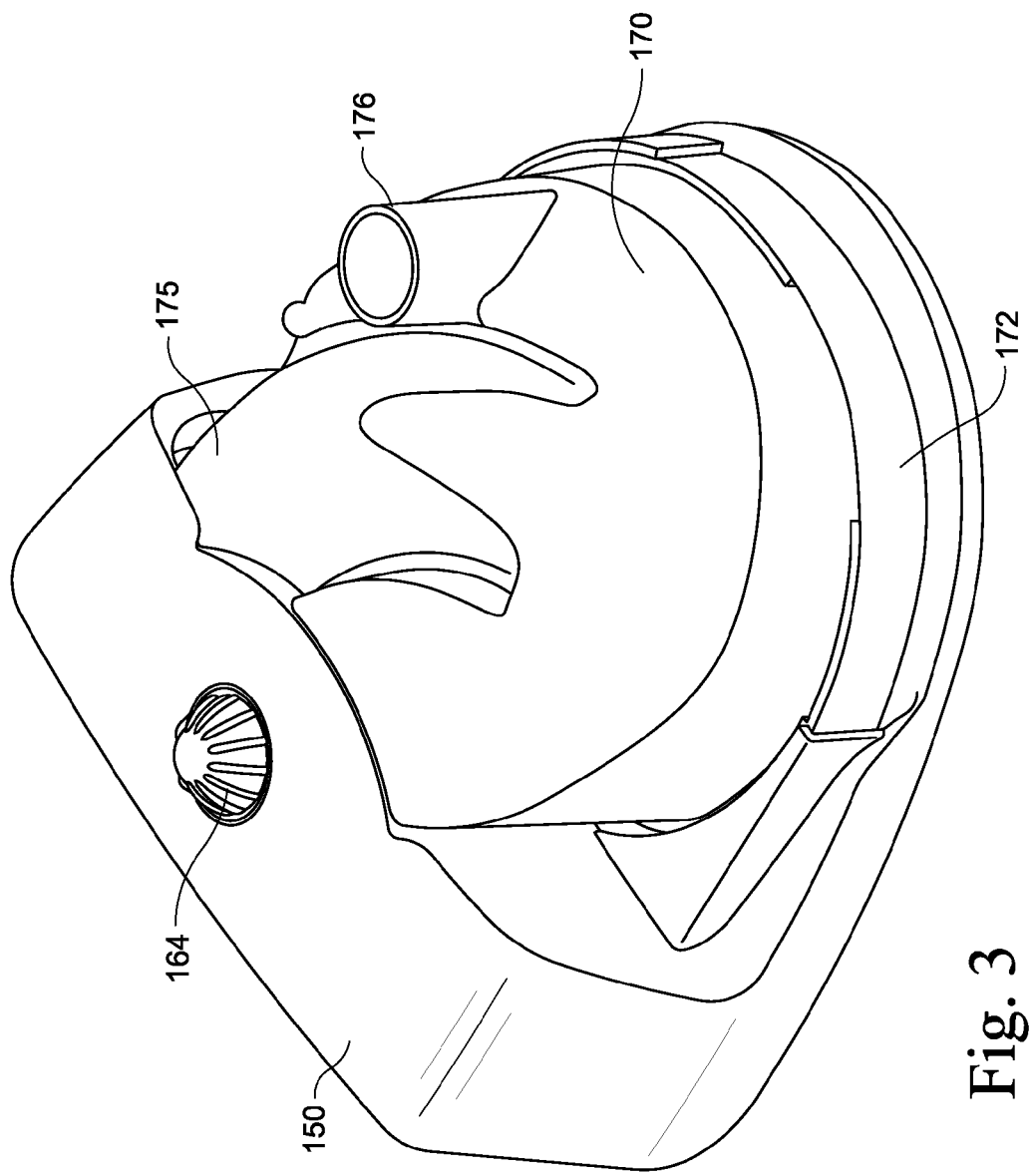
FIG. 3 shows the humidifier unit.
Figure 4:
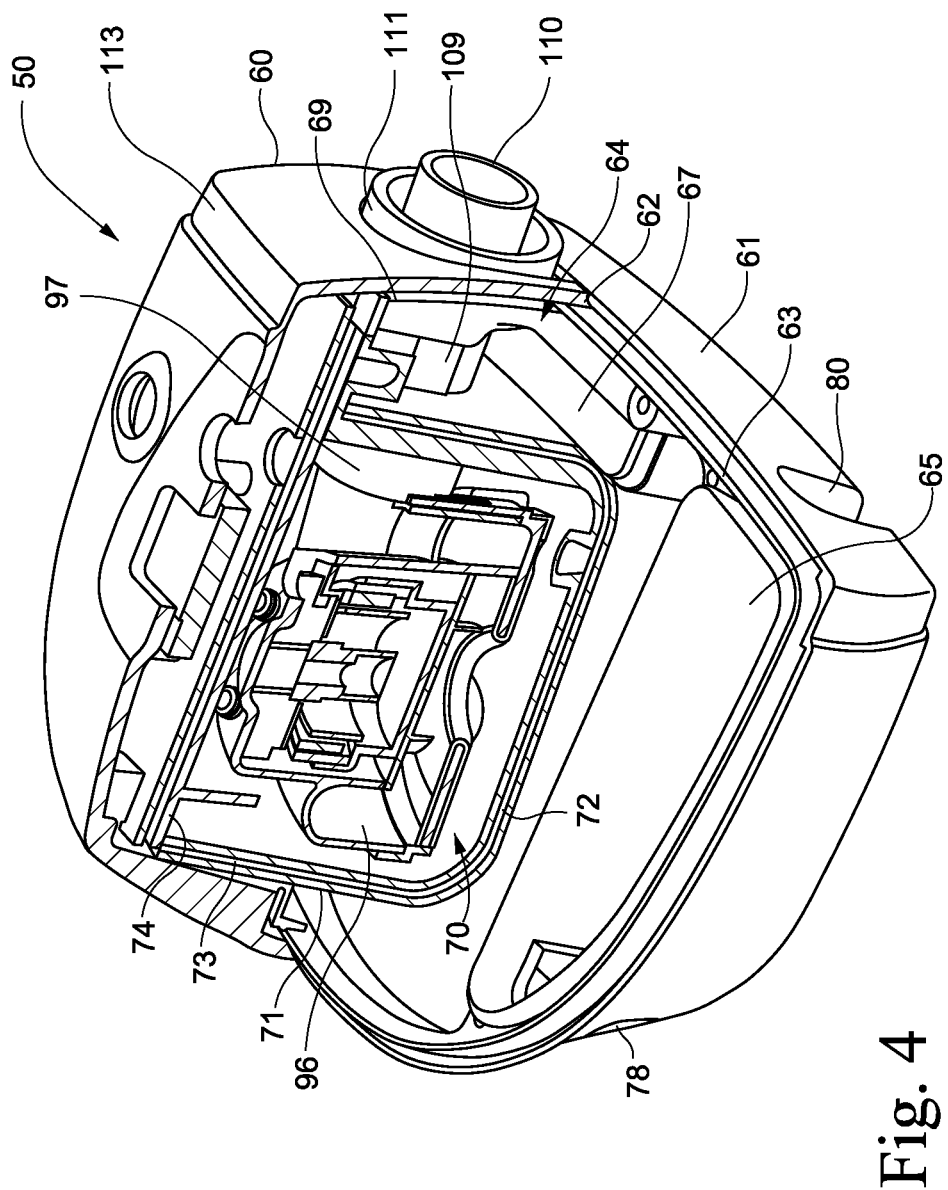
FIG. 4 is a cutaway view of the flow generator.

The periphery of the base flange 172 is dimensioned to slide into engagement with the wall 165 of the base unit and beneath the flange 166 to engage the tank with the base unit, and the tank cover 170 is provided with a cylindrical air inlet 175 extending from its side wall. The inlet 175 is dimensioned to fit sealingly within the recess 167 when the tank is engaged with the base unit as described above and as shown in FIG. 3.

An air outlet 176 extends upwardly from the roof of the cover 170 for connection with an air hose for the delivery of humidified air to the patient.

The metal base 171 seats within the base flange 172 which is provided with a central aperture, so that the bottom of the metal base 171 is exposed to contact the pad 163 when the tank is engaged with the base unit. The metal base 171 is thus heated by the heating element of the base unit. To assist in achieving good heat transfer between the pad 163 and the base 171, the former is resiliently biased upwardly, for example by means of a spring or springs (not shown). This has the further advantage of providing for positive retention of the tank in the base unit, by providing around the central aperture in the base flange, a downwardly directed rim (not shown) which will initially depress the heating plate as the tank is moved into position on the base unit, and which forms a central space into which the heating plate moves under its spring pressure, upon full engagement of the tank with the base unit.

In alternative embodiments not illustrated here, the tank may be provided with locking detents for retention on the base unit.

The lower edge of the cover 170 and the inner edge of the base flange 172 are provided with bayonet type engagement formations 177 and 178 respectively, so the tank components can be assembled and disassembled simply by relative rotation of the cover and the base flange. To assist in this operation, a peripheral groove 179 is provided in the base of the base flange 172, and this groove is interrupted at intervals by finger-engaging bridges 180. The inner wall of the groove 179 protects the user's fingers against accidental contact with the metal base 171, in case removal of the cover is carried out while the base is still hot.

The tank is intended to be filled via the air outlet 176, and the apparatus may be provided with a filling bottle with a spout dimensioned for a convenient fit with that outlet. Such a bottle may be provided with a spout of the kind incorporating an air bleed passage which will allow the tank to fill to the correct predetermined height.

In alternative embodiments, other filling arrangements may be employed. The correct filling height is also indicated by filling level graduations 184 scribed or otherwise marked on the wall of the cover 170.

Figure 16:
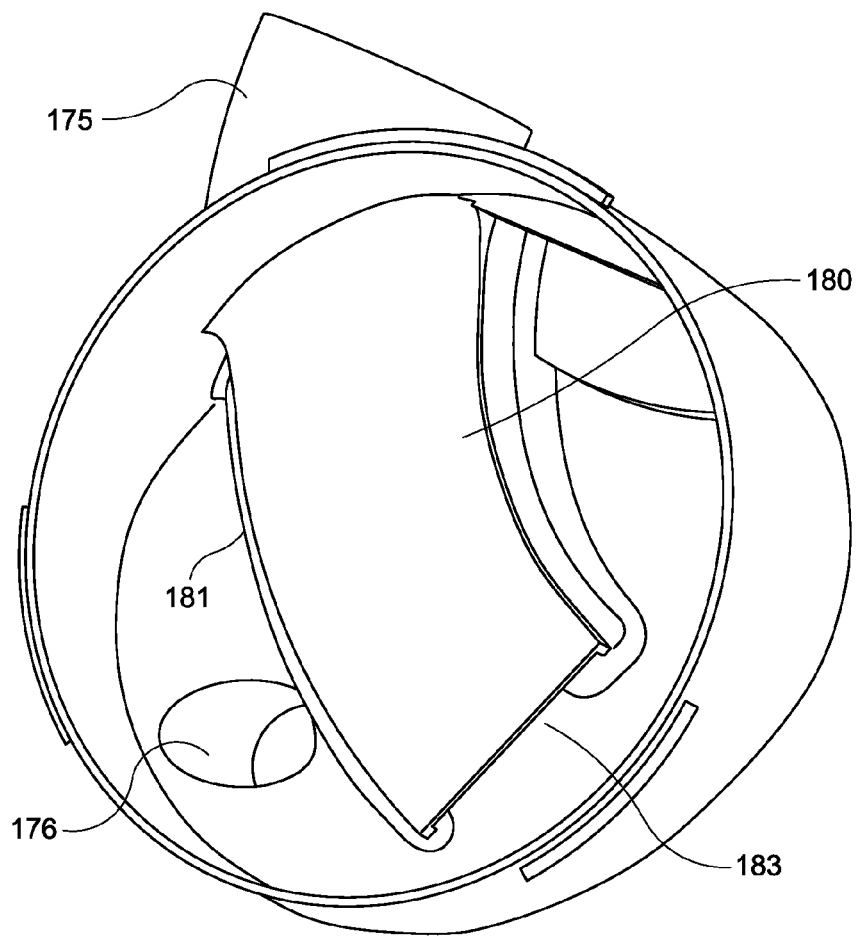
FIG. 16 is an underneath view of the tank cover.

As will be seen in FIG. 16, the air inlet 175 of the cover 170 extends within the cover in the form of an arcuate passage 181, to open to the interior of the cover at a point beyond, in the direction of air flow, the outlet 176. The open end 183 of the passage 181 is directed obliquely towards the inner wall of the cover. The outlet 176 is, furthermore, between the convexly curved side of the passage 181. This configuration has several important consequences.

Firstly the curvature of the passage 181 and the oblique orientation of its outlet 183 will induce a swirling action on the air mass within the tank, as the air moves around the tank to escape from the outlet 176. This swirling action will enhance the uptake of water vapour from the water contained in the tank.

Secondly the configuration minimises the risk of water from the tank flowing back into the air inlet passage should the tank be tilted while containing water. Whenever the orientation of the tank is such that the air outlet 176 is below the outlet 183, water will flow into the air outlet before it will flow into the inlet passage, and whenever the air outlet 176 is above the outlet 183, then except in the case of inversion of the tank, water will not escape via the arcuate passage 181 unless the tank has been filled with a volume of water which is greater than that which is contained within the sector of the tank below a tangent to the convex surface of the passage 181. This can be avoided by appropriate setting of the heights of the filling level graduations 184.

Should water escape into the passage 181 due to inversion of the humidifier while it is engaged with the flow generator, its path to the air flow passage 160 will be blocked by the dam formed by the face of the recess 167, which will then be below the air flow passage 160.

Figure 17:
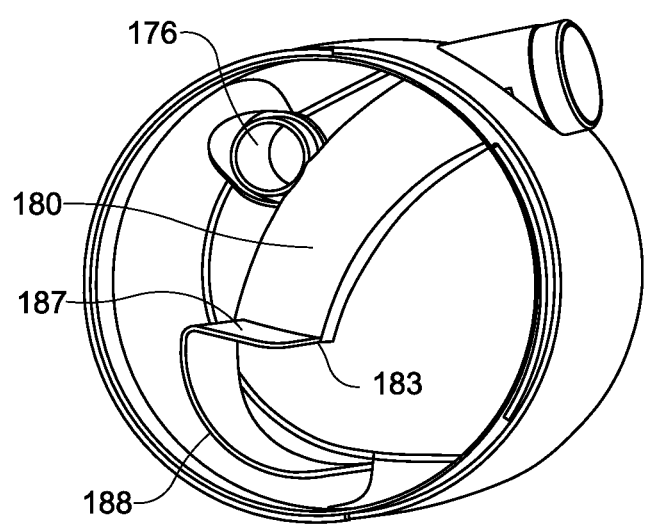
FIG. 17 is an underneath view of a modified tank cover.
Figure 18:
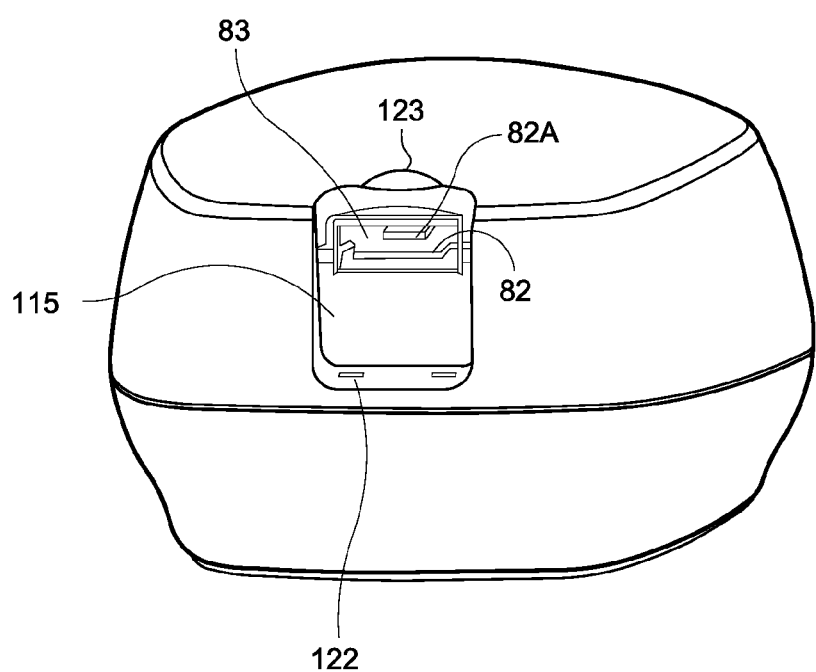
FIG. 18 shows an exemplary modular connector arrangement.
Figure 19A:
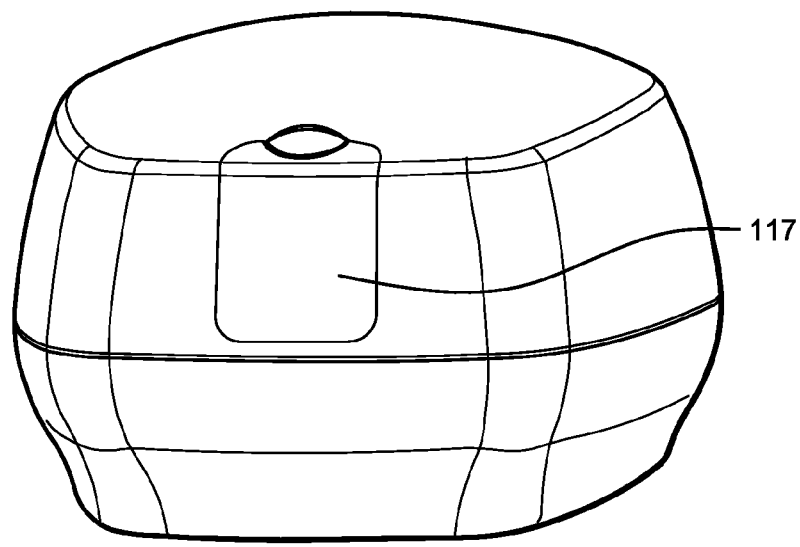
FIG. 19A shows an exemplary modular connector arrangement with the exemplary cover of FIG. 19.
Figure 19:
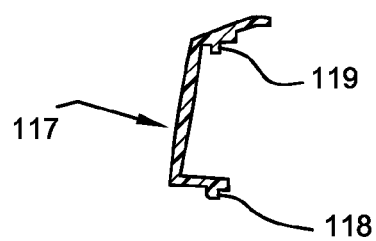
FIG. 19 shows an exemplary cover for an exemplary modular connector arrangement.

FIG. 17 shows a modified form of tank cover in which a downwardly extending wall 187 is provided across the end of the arcuate passage 181, this wall extending in a curved wall 188 beyond the outlet 183. The curved wall 188 assists in the formation of a swirling air flow within the tank, while both walls 187 and 188 tend to protect the outlet 183 against wave action within the tank during transport.

Figure 14:
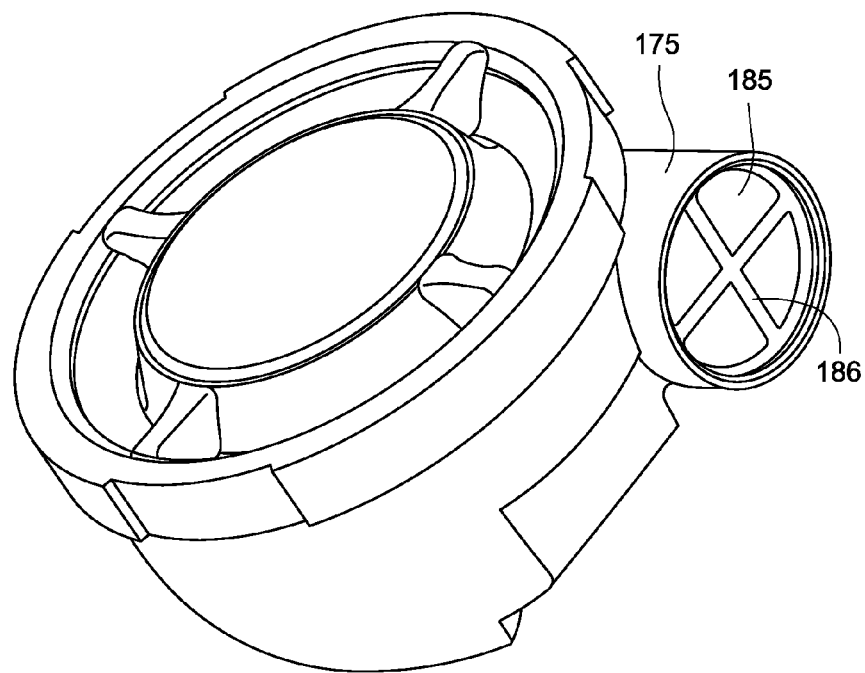
FIG. 14 is an underneath view of the tank showing an alternative valve.
Figure 15:
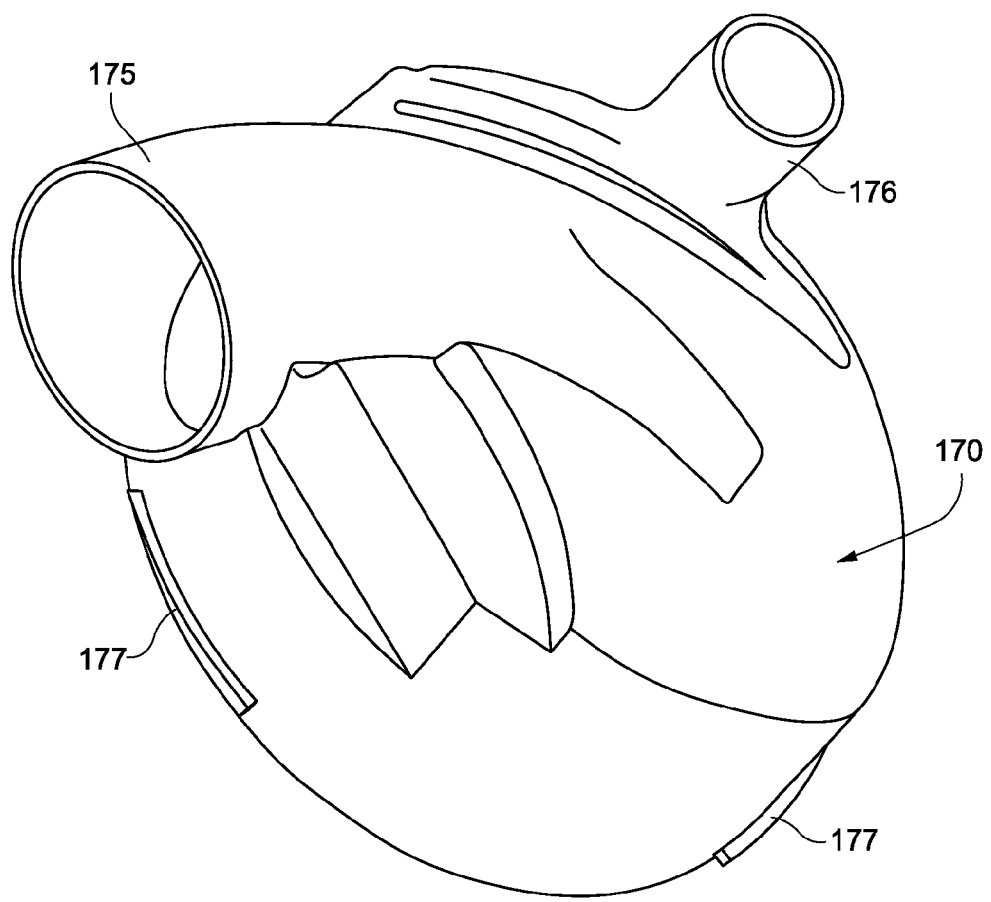
FIG. 15 is a view of the tank cover.

If desired, further security against backflow can be provided by locating a non-return valve at an appropriate point. An example of this is shown in FIG. 14, where a valve comprising a flexible membrane 185 supported on a spider 186 is placed in the mouth of the tank air inlet 175.

In the illustrated embodiment the arcuate passage 181 is shown as a low profile passage of substantially rectangular cross-section. An alternative approach is to continue this passage as a cylindrical passage having a diameter similar to that of the air passage leading from the flow generator to the humidifier. The advantage of this will be to avoid the introduction of impedance to the flow of air through the humidifier. Generally speaking it is desirable to minimise pressure drop through the humidifier, to avoid interfering with diagnostic or monitoring functions in the flow generator, for example the detection of snoring, which require the detection of sound transmitted back through the system from the patient.

The enhanced uptake of water vapour achieved by inducing the swirling of air as it passes through the tank enables, in an alternative embodiment of the invention, the elimination of the heating of the water in the tank 152. In such an embodiment the heating element and its controls, and the heat transfer components including the pad 163 and the metal tank base 171 are eliminated, and the humidifier becomes a simpler, passive, device.

FIGS. 18 to 21 show various forms of modular data connections foreshadowed earlier, utilizing the connector aperture 83 in the rear of the flow generator housing.

The connector aperture 83 is provided in the wall of a rectangular recess 115. An arcuate depression 123 is provided in the upper surface of the unit above the recess 115 to facilitate removal of closure elements from the depression, as described below.

Where the flow generator in question is not intended to be employed with any data connection, the connector aperture 83 is closed off by a blank closure element 117, shaped to fit into the recess 115. This element snaps into the recess by means of lower tabs 118 and an upper tab 119 which fit corresponding depressions such as 122 in the walls of the recess 115, to close the connector aperture 83 and conform to the contours of the surrounding surface of the unit.

Figure 20:
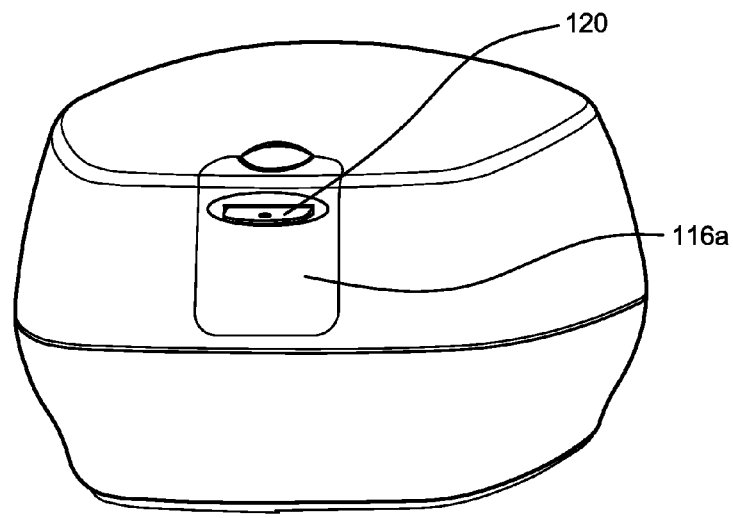
FIG. 20 shows an exemplary modular connector arrangement.
Figure 21:
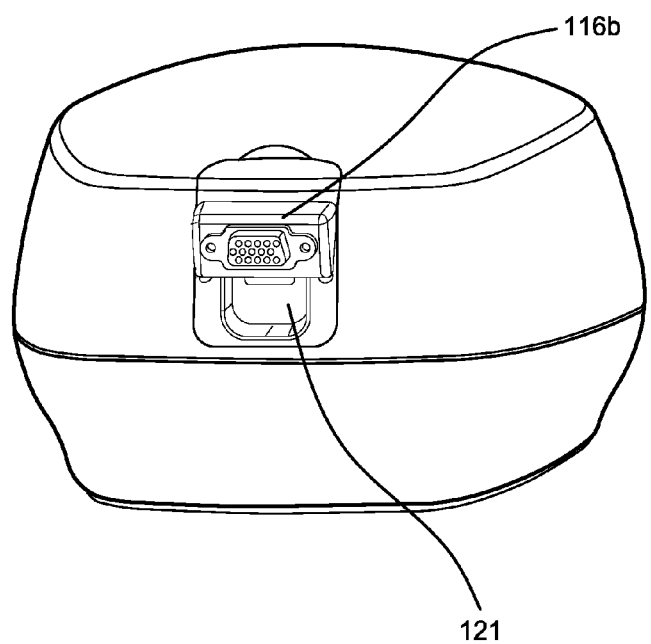
FIG. 21 shows an exemplary modular connector arrangement.

Complementarily shaped closure elements can be provided for the reception of different kinds of data devices. Shown in FIG. 20 is an element 116a provided with a slot for the reception of a smart card 120. The element 116a or the printed circuit board itself may carry the necessary smart card socket. Shown in FIG. 21 is an element 116b provided with a DB type data socket. In this case the element 116b is contoured to provide a lower front recess 121 to facilitate gripping of the associated plug.

Other forms of element 116 can be provided to enable the connection of devices such as memory cards and pre-programmed devices as required. This facility furthermore enables a wide range of devices to be integrated with the apparatus in modular fashion, for example a clock display which may utilise the system clock contained in the flow generator controller, a voice activation unit, oximetry, ECG and other diagnostic aids, a sound recorder, a light.

It is emphasised that the forgoing disclosure has sought to describe many innovations in flow generator and humidifier design, and it is foreshadowed that these will be the subject of separate claims to protection in applications claiming the priority of this document.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

The invention claimed is:

1. A humidifier comprising:
   a base unit configured to attach to and detach from a flow generator, said base unit comprising:
   an engagement face adapted to face a corresponding engagement face of the flow generator;
   at least one tongue located on the engagement face that is adapted to move vertically and adapted to be resiliently urged downward to engage at least one slot of the flow generator;
   an air flow passage configured to receive an air connector of the flow generator;
   an electrical connector, for engagement with a mating electrical connector on the flow generator, the electrical connector of the humidifier adapted to provide electrical power to the humidifier from the flow generator;
   a pad that stands proud of a surrounding base surface and is resiliently biased upwardly; and
   a heating element to heat the pad;
   and
   a tank to receive water, said tank being adapted to be slidable relative to the base unit; the tank comprising:
   a cover;
   a base sealingly connected to the cover;
   an air inlet passage extending from a side wall of the tank; and
   an air outlet provided to a roof of the cover,
   wherein:
   a bottom of the base is exposed to contact the pad as the tank is engaged with the base unit,
   at least one liquid filling height is indicated by a filling level graduation marked on a wall of the tank,
   the air inlet passage extends so that it opens in the interior of the tank at a point beyond, in the direction of air flow, a center of the air outlet,
   the air inlet passage and the air outlet are oriented so that air flows through the air inlet passage in a direction perpendicular to a direction in which the air flows through the air outlet, and
   a vertical offset is provided between the air flow passage of the base unit and the air inlet passage,
   a water collection point is located adjacent and outside an entry side of the air inlet passage of the tank.

2. The humidifier of claim 1, wherein the water collection point is located between the air inlet passage of the tank and a portion of the air flow passage configured to receive the air connector of the flow generator.

3. The humidifier of claim 1, wherein the electrical connector is configured to provide data to the humidifier.

4. The humidifier of claim 1, wherein the tank is configured to be filled via the air outlet.

5. The humidifier of claim 1, wherein, in at least two tilted positions of the tank, at least a portion of the air outlet is below the open end of the air inlet passage, such that water will flow through the air outlet before it will flow into the air inlet passage, and wherein in a normal operating position, when the air outlet is above the open end of the air inlet passage, water will not escape via the air inlet passage unless the tank has been over-filled.

6. The humidifier of claim 5, wherein a maximum filling level graduation of the filling level graduation is marked on the wall of the tank, the maximum filling level graduation being lower than a lowest level of the air inlet passage.

7. The humidifier of claim 1, wherein the engagement face of the humidifier includes a flange configured to seat in a corresponding recess in the engagement face of the flow generator.

8. The humidifier of claim 1, wherein the pad is biased upwardly by one or more springs.

9. The humidifier of claim 1, wherein the air flow passage is provided with a sealing device configured to sealingly receive the air connector of the flow generator.

10. The humidifier of claim 1, wherein the air inlet passage has a diameter substantially equal to that of the air passage leading from the flow generator to the humidifier, wherein an orientation of the open end of the air inlet passage is arranged to induce swirling action on air within the tank, as air moves around the tank to exit from the open end of the air inlet passage in order to enhance uptake of water vapor from water contained in the tank, and wherein a portion of the air inlet passage adjacent the sidewall of the tank has a cylinder-type shape.

11. The humidifier of claim 1, wherein an axis of the air inlet passage of the tank and an axis of a portion of the air flow passage configured to receive the air connector of the flow generator are vertically offset.

12. The humidifier of claim 1, wherein the tank further comprises an inner wall extending downward from the cover and an end of the air inlet passage inside the tank is directed towards the inner wall, and a portion of the inner wall is curved.

13. The humidifier of claim 12, wherein an orientation of the end of the air inlet passage proximal the inner wall is arranged to induce swirling action on air within the tank, as air moves around the tank to exit from the end of the air inlet passage proximal the inner wall in order to enhance uptake of water vapor from water contained in the tank, and the cover is comprised of transparent material.

14. The humidifier of claim 1, wherein the humidifier comprises a plurality of tongues located on the engagement face that are adapted to move vertically and adapted to be resiliently urged downward to engage a plurality of slots of the flow generator.

15. The humidifier of claim 1, wherein at least a portion of the air flow passage is lower than the air inlet passage in the normal orientation of the humidifier.

16. The humidifier of claim 1, wherein a sealing gasket is provided between the cover and the base of the tank.

17. A breathable gas supply apparatus for use in continuous positive airway pressure (CPAP) treatments, the apparatus comprising:

a humidifier according to claim 1; and a flow generator that has an engagement face to face the engagement face of the humidifier, the flow generator comprising:

an external case of rigid plastic material comprising a top case and a bottom case, a lower edge of the top case being stepped and flanged to mate with a periphery of the bottom case;

an air connector projecting away from the engagement face of the flow generator and being in communication with the air flow passage of the humidifier;

a slot configured to receive a data card, the slot being provided in a wall of the external case;

an LCD screen visible through the top case by which a user can set operating parameters of the apparatus;

a chassis positioned within the case, the chassis including a peripheral wall and a fan cavity;

a printed circuit board carrying electronic control components of the breathable gas supply apparatus, the printed circuit board being positioned in a space formed between the chassis and the top of the top case;

an air inlet formed in a wall of the external case;

an air inlet passage that communicates with the air inlet and opens to a space at least partly surrounding the fan cavity; and an inlet tube configured to direct air from the space at least partly surrounding the fan cavity to an interior of the fan cavity; and a fan mounted in the fan cavity, the fan comprising:

a fan housing including a cover and a base;

a motor mounted within the fan housing;

a coaxial impeller mounted within the fan housing;

an air inlet in a floor of the base on an axis of the impeller; and an air outlet, wherein cavities in the cover and base of the fan housing form a volute which leads from the impeller to the fan air outlet, and the fan air outlet is connected to the air connector via a coupling member.

18. The breathable gas supply apparatus of claim 17, wherein the top case of the flow generator comprises at least one input device connected to the electronic control components of the printed circuit board.

19. The breathable gas supply apparatus of claim 17, further comprising a cover configured to be removably attached to the wall of the external case and cover a portion of the wall around the slot when attached to the wall.

20. The breathable gas supply apparatus of claim 19, wherein the cover includes an opening configured to provide access to the slot in the wall of the external case.

21. The breathable gas supply apparatus of claim 17, further comprising an air hose for the delivery of humidified air to a patient connected to the air outlet of the humidifier.

22. A method of humidifying pressurized gas comprising:

receiving pressurized gas from ambient or an external source in an air flow passage positioned at a first position within a base unit of a humidifier, the first position being proximate an engagement face of the base unit that is configured to interface with a flow generator;

directing the received pressurized gas from the first position within the base unit to an air inlet passage of a tank at a second position that is axially offset from the air flow passage at the first position, the tank being at least partly contained within the base unit and holding liquid;

exposing the pressurized gas to the liquid in the tank to humidify the pressurized gas; and collecting liquid at a liquid collection point between the first and second positions if liquid leaks out of the tank through the air inlet passage.

23. The method of claim 22, wherein gas at the first position flows in a first direction and gas at the second position flows in a second direction, and the first and second directions are substantially parallel to a horizontal plane.

24. The method of claim 22, wherein a flow of gas at the first position and the second position is substantially parallel to a horizontal plane.

25. The method of claim 24, further comprising heating the liquid in the tank and exposing the pressurized gas to vaporized liquid.

26. The method of claim 22, wherein relative locations of the first and second positions inhibit the liquid in the tank from reaching the first position when the humidifier is tilted from the normal upright operating orientation.

27. The method of claim 26, wherein a shape of the tank inhibits the liquid in the tank from reaching the first position when the humidifier is tilted from the normal upright operating orientation.

28. The method of claim 27, wherein components within the tank inhibit the liquid in the tank from reaching the first position when the humidifier is tilted from the normal upright operating orientation.

29. The method of claim 27, wherein the relative locations of the first and second positions and the shape of the tank cooperate to form a tiered liquid back flow prevention arrangement in which the shape of the tank provides a first level of liquid back flow prevention and the relative locations of the first and second positions provide a second level of liquid back flow prevention.

30. The method of claim 22, further comprising delivering the humidified pressurized gas to a gas outlet extending upwardly from a roof of the tank.

\* \* \* \* \*